United States Patent
Hess et al.

(10) Patent No.: US 9,233,106 B2
(45) Date of Patent: Jan. 12, 2016

(54) INHIBITION OF BETA-AMYLOID PEPTIDE AGGREGATION

(75) Inventors: George P. Hess, Ithica, NY (US); Moataz M. Gadalla, Ithica, NY (US)

(73) Assignee: CORNELL RESEARCH FOUNDATION, INC., Ithaca, NY (US)

( * ) Notice: Subject to any disclaimer, the term of this patent is extended or adjusted under 35 U.S.C. 154(b) by 1732 days.

(21) Appl. No.: 12/373,456

(22) PCT Filed: Jul. 12, 2007

(86) PCT No.: PCT/US2007/073349
§ 371 (c)(1),
(2), (4) Date: Nov. 20, 2009

(87) PCT Pub. No.: WO2008/008884
PCT Pub. Date: Jan. 17, 2008

(65) Prior Publication Data
US 2010/0069468 A1 Mar. 18, 2010

Related U.S. Application Data

(60) Provisional application No. 60/807,195, filed on Jul. 12, 2006.

(51) Int. Cl.
*A61K 31/46* (2006.01)
*A61K 31/55* (2006.01)
*A61K 31/495* (2006.01)
*C12N 15/115* (2010.01)

(52) U.S. Cl.
CPC .............. *A61K 31/46* (2013.01); *A61K 31/495* (2013.01); *A61K 31/55* (2013.01); *C12N 15/115* (2013.01); *C12N 2310/16* (2013.01); *C12N 2320/11* (2013.01)

(58) Field of Classification Search
CPC ...... A61K 31/46; A61K 31/495; A61K 31/55
See application file for complete search history.

(56) References Cited

U.S. PATENT DOCUMENTS

| | | | |
|---|---|---|---|
| 5,227,385 A * | 7/1993 | Caldwell et al. ...... | A61K 31/435 514/304 |
| 6,077,848 A * | 6/2000 | Wynn et al. .................... | 514/304 |
| 6,683,090 B1 | 1/2004 | Balestra et al. | |
| 2001/0055607 A1* | 12/2001 | Levin ............................ | 424/435 |
| 2004/0171635 A1* | 9/2004 | Archer et al. ................. | 514/304 |

OTHER PUBLICATIONS

Farlow MR (2004) NMDA receptor antagonists: a new therapeutic approach for Alzheimer's disease. Geriatrics, 59(6):22-27 (abstract only).*
Marotta CA et al. (1992) Molecular and cellular biology of Alzheimer amyloid. J. Mol. Neurosci. 3:111-125.*
Mash DC et al. (2003) Cocaine abusers have an overexpression of alpha-synuclein in dopamine neurons. J. Neurosci. 23(7):2564-2571.*
Soto C et al. (1996) Inhibition of Alzheimer's amyloidosis by peptides that prevent beta-sheet conformation. Biochem. Biophys. Res. Comm. 226:672-680.*
Karran E et al. (2011) The amyloid cascade hypothesis for Alzheimer's disease: an appraisal for the development of therapeutics. Nat. Rev. Drug Discov. 10(9):698-712.*
Liu SJ et al. (2003) Alzheimer-like phosphorylation of tau and neurofilament induced by cocaine in vivo. Acta Pharmacol. Sin. 24(6):512-518.*
Vickers JC (2002) A vaccine against Alzheimer's disease, Developments to date. Drugs Aging, 19(7):487-494.*
Zhou et al. "Norepinephrine Transporter Inhibitors and Their Therapeutic Potential," Drugs Future 29(12):1235-1244 (2004).
Hess et al. "Reversing the Action of Noncompetitive Inhibitors (MK-801 and Cocaine) on a Protein (Nicontinic Acetylcholine Receptor)-Mediated Reaction," Biochemistry 42:6106-6114 (2003).
Chen et al. "Mechanism-Based Discovery of Small Molecules that Prevent Noncompetitive Inhibition by Cocaine and MK-801 Mediated by Two Different Sites on the Nicotinic Acetylcholine Receptor," Biochemistry 43:10149-10156 (2004).
Ylera et al. "Selection of RNA Aptamers to the Alzheimer's Disease Amyloid Peptide," Biochemical and Biophysical Research Communications 290:1583-1588 (2002).
Cregan et al. [(S)-Alpha-Phenyl-2-Pyridine-Ethanamine Dihydrochloride], A Low Affinity Uncompetitive N-Methyl-DAspartic Acid Antagonist, Is Effective in Rodent Models of Global and Focal Ishemia,' The Journal of Phamacology and Experimental Therapeutics 283(3):1412-1424 (1997).
Gadalla et al. "Discovery of a Regulatory Site on Beta-Amyloid Peptides," Cornell Undergraduate Spring Research Forum (Apr. 19, 2006) (abstract only).
Soto et al., "Amyloid Inhibitors and Beta-Sheet Breakers," (Chapter 18), Subcellular Biochemistry 38:351-364 (2005).
Talaga, "Beta-Amyloid Aggregation Inhibitors for the Treatment of Alzheimer's Disease: Dream or Reality?" Mini Reviews Medicinal Chemistry 1:175-186 (2001).
International Search Report and Written Opinion for Corresponding PCT/US07/73349 (mailed Apr. 15, 2008).

* cited by examiner

*Primary Examiner* — Kimberly A. Ballard
(74) *Attorney, Agent, or Firm* — LeClairRyan, a Professional Corporation

(57) ABSTRACT

The present invention relates to methods of using cocaine-binding-site ligands and cocaine-binding-site RNA aptamers to treat or prevent Alzheimer's Disease and to reduce or prevent aggregation of beta-amyloid peptides in a subject.

11 Claims, 5 Drawing Sheets

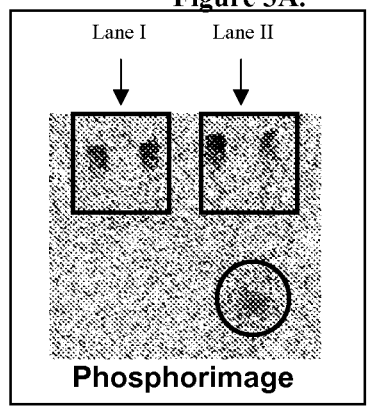
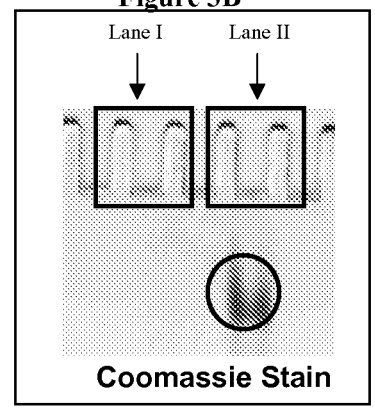
Figures 3A-B

INHIBITION OF BETA-AMYLOID PEPTIDE AGGREGATION This application claims benefit of U.S. Provisional Patent Application Ser. No. 60/807,195, filed Jul. 12, 2006, which is hereby incorporated by reference in its entirety.

The subject matter of this application was made in part with government support under National Institutes of Health Grant No. R25 GM 66910. The U.S. Government may have certain rights.

FIELD OF THE INVENTION

The present invention relates to methods of using cocaine-binding-site ligands and cocaine-binding-site RNA aptamers to treat or prevent Alzheimer's Disease and to reduce or prevent aggregation of beta-amyloid peptides involved in Alzheimer's Disease in a subject.

BACKGROUND OF THE INVENTION

It is estimated that 24.3 million people have dementia today, with 4.6 million additional cases of dementia occurring every year (one new case every 7 seconds) (Ferri et al., "Global Prevalence of Dementia: A Delphi Consensus Study," *Lancet* 366:2112-2117 (2005)). The numbers of people affected worldwide are expected to double every 20 years to reach 81.1 million by 2040 (Ferri et al., "Global Prevalence of Dementia: A Delphi Consensus Study," *Lancet* 366:2112-2117 (2005)). An estimated 4.5 million Americans had Alzheimer's Disease in 2000 (Hebert et al., "Alzheimer Disease in the U.S. Population: Prevalence Estimates Using the 2000 Census," *Archives of Neurology* 60:1119-1122 (2003)). The number of Americans with Alzheimer's has more than doubled since 1980 (Hebert et al., "Alzheimer Disease in the U.S. Population: Prevalence Estimates Using the 2000 Census," *Archives of Neurology* 60:1119-1122 (2003)) and will continue to grow; by 2050 the number of individuals with Alzheimer's is expected to be more than 11.3 million in the US alone (Hebert et al., "Alzheimer Disease in the U.S. Population: Prevalence Estimates Using the 2000 Census," *Archives of Neurology* 60:1119-1122 (2003)). From the time of diagnosis, people with Alzheimer's Disease survive about half as long as those of similar age without dementia (Larson et al., "Survival After Initial Diagnosis of Alzheimer Disease," *Annals of Internal Medicine*, 501-509 (2004)). The average survival time is affected by the age at diagnosis and the severity of other medical conditions (Larson et al., "Survival After Initial Diagnosis of Alzheimer Disease," *Annals of Internal Medicine*, 501-509 (2004)). National direct and indirect annual costs of caring for individuals with Alzheimer's Disease are at least U.S. $100 billion (Ernst et al., "The U.S. Economic and Social Costs of Alzheimer's Disease Revisited," *Am. J. Public Health* 84:1261-1264 (1994)).

Alzheimer's Disease is an age-related neurodegenerative disorder that is characterized by progressive loss of memory and deterioration of higher cognitive function (Kar et al., "Interactions Between β-Amyloid and Central Cholinergic Neurons: Implications for Alzheimer's Disease," *J. Psychiatry Neurosci.* 29:427-441 (2004)). Alzheimer's Disease is not a normal part of aging. The brain of an individual with the disease exhibits extracellular plaques and intracellular neurofibrillary tangles. The extracellular plaques consist of aggregates of 39-42 amino-acid peptides known as β-amyloid peptides (Aβ) (Selkoe, D. J. "Cell Biology of Protein Misfolding: The Examples of Alzheimer's and Parkinson's Diseases," *Nat. Cell Biol.* 6:1054-1061 (2004)). The Aβ peptides are formed by enzyme-(β-secretase) catalyzed degradation of transmembrane proteins of unknown function called Amyloid Precursor Proteins (APP) (Saido et al., "Metabolism of Amyloid β Peptide and Pathogenesis of Alzheimer's Disease. Toward Presymptomatic Diagnosis, Prevention and Therapy," *Neurosci. Res.* 54:235-253 (2006)). The aggregated Aβ peptides in plaques exert toxic effects on a wide variety of cells in the nervous system. Neurofibrillary tangles are formed intracellularly in the neuron cell bodies. These tangles consist of intracellular aggregates of hyperphosphorylated tau-protein (Grundke-Iqbal et al., "Abnormal Phosphorylation of the Microtubule-Associated Protein τ (tau) in Alzheimer Cytoskeletal Pathology," *Proc. Natl. Acad. Sci. USA* 83:4913-4917 (1986)). Tau (τ) protein is a microtubule-associated protein important for the neuron cytoskeleton.

Currently, only a handful of agents are approved by the Food and Drug Administration for treatment of Alzheimer's Disease. These agents mainly target the synthesis, release, or degradation of neurotransmitters in the cholinergic system; but have demonstrated only modest effects in modifying the clinical symptoms for relatively short periods, and none has shown a clear effect on the progression of the disease. Finding a treatment that delays the onset of Alzheimer's by five years could reduce the number of individuals with Alzheimer's Disease by nearly 50 percent after 50 years (Brookmeyer et al., "Projections of Alzheimer's Disease in the United States and the Public Health Impact of Delaying Disease Onset," *Am. J. Public Health* 88:1337-1342 (1998)). There is a need for new Alzheimer's Disease therapeutics.

The present invention is directed to overcoming these and other deficiencies in the art.

SUMMARY OF THE INVENTION

One aspect of the present invention relates to a method of treating or preventing Alzheimer's Disease in a subject by using a cocaine-binding-site ligand. This method involves administering to the subject a cocaine-binding-site ligand under conditions effective to treat or prevent Alzheimer's Disease in the subject. The cocaine-binding-site ligand used in this method is one that binds to a cocaine-binding site of a beta-amyloid peptide.

Another aspect of the present invention relates to a method of reducing or preventing aggregation of beta-amyloid peptides in a subject by using a cocaine-binding-site ligand. This method involves administering to the subject a cocaine-binding-site ligand under conditions effective to reduce or prevent aggregation of beta-amyloid peptides in the subject. The cocaine-binding-site ligand used in this method is one that binds to a cocaine-binding site of a beta-amyloid peptide.

An additional aspect of the present invention relates to a method of treating or preventing Alzheimer's Disease in a subject by using a cocaine-binding-site RNA aptamer. This method involves administering to the subject a cocaine-binding-site RNA aptamer under conditions effective to treat or prevent Alzheimer's Disease in the subject. The RNA aptamer used in this method is one that binds to a cocaine-binding site of a beta-amyloid peptide.

Yet another aspect of the present invention relates to a method of reducing or preventing aggregation of beta-amyloid peptides in a subject by using a cocaine-binding-site RNA aptamer. This method involves administering to the subject a cocaine-binding-site RNA aptamer under conditions effective to reduce or prevent aggregation of beta-amyloid peptides in the subject. The RNA aptamer used in this method is one that binds to a cocaine-binding site of a beta-amyloid peptide.

The present invention uses various cocaine-binding-site ligands (e.g., small organic molecules) and cocaine-binding-site RNA aptamers that bind with high affinity to a site (e.g., a cocaine-binding site) on beta-amyloid peptides and prevent their aggregation. Prior to the present invention, there was no report of a small organic compound that was non-toxic, able to cross the blood barrier, able to bind to a specific site on beta-amyloid peptides, and capable of inhibiting their aggregation. The cocaine-binding-site ligands and RNA aptamers of the present invention have the potential to prevent all known key pathological processes in Alzheimer's Disease, forming a unique trifunctional class of compounds that prevent beta-amyloid aggregation, beta-amyloid induced inhibition of the nicotinic acetylcholine receptor, and beta-amyloid-induced tau phosphorylation; thus preventing the three major processes thought to be responsible for Alzheimer's Disease pathology.

Ligands that (i) bind to amyloid peptides preventing their aggregation, (ii) alleviate inhibition of the nicotinic acetylcholine receptor by the amyloid peptides, and (iii) inhibit Aβ-induced tau phosphorylation, would provide a unique class of compounds that could potentially provide novel Alzheimer's Disease therapeutics. Such compounds have the potential to prevent Aβ aggregation, Aβ-induced inhibition of the nicotinic acetylcholine receptor, and Aβ-induced tau phosphorylation, preventing the three major processes thought to be responsible for Alzheimer's Disease pathology.

BRIEF DESCRIPTION OF THE DRAWINGS

FIG. 1A depicts whole-cell current recording from muscle type nicotinic acetylcholine receptor expressed in BC$_3$H1 cells treated with the β-amyloid-peptide-binding RNA aptamer, B55. The cell-flow technique with a 10-ms time resolution was used (Udgaonkar et al., "Chemical Kinetic Measurements of a Mammalian Acetylcholine Receptor by a Fast-Reaction Technique," *Proc. Nat. Acad. Sci. USA* 84:8758-8762 (1987), which is hereby incorporated by reference in its entirety)). Experiments were conducted at ~22° C., −60 mV, and pH 7.4. The currents were induced by application of 100-μM carbamoylcholine only (lighter rising and falling line) or by a 2-second preincubation of the cells with 1-μM aptamer B55 followed by coapplication of the aptamer (at the same concentration used in preincubation) with 100-μM carbamoylcholine for 6 s (darker rising and falling line). The upper traces parallel to the abscissa represent the current amplitudes corrected for receptor desensitization that occurs during the rising phase. FIG. 1B represents the dissociation constant of the B55 aptamer for the nicotinic acetylcholine receptor. $A_O$ is the maximum current amplitude in the presence of 100-μM carbamoylcholine, and $A_I$ the maximum current amplitude in the presence of the same concentration of carbamoylcholine and different concentrations of aptamer B55. The whole-cell current was corrected for receptor desensitization. Each data point is the average of 2-4 measurements with at least two cells. The data were plotted according to $$\frac{A_O}{A_I} = 1 + \frac{[I]}{K_I}$$

and gave a value for the dissociation constant of aptamer B55, $K_1$, of 1.2±0.1 μM.

Figure 2:
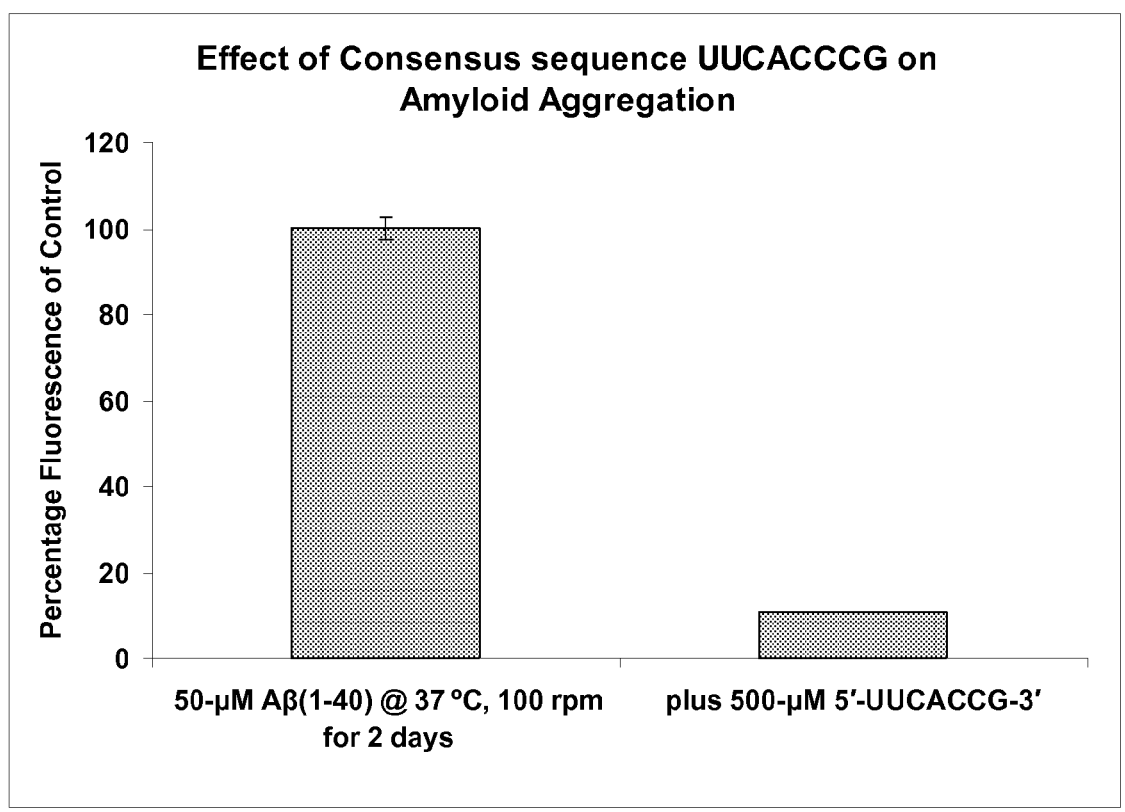

FIG. 2 depicts inhibition of Aβ(1-40) peptide aggregation by the aptamer consensus sequence, UUCACCCG, oligonucleotide. 50-μM Aβ(1-40) solutions were made in 50-mM sodium phosphate, 100-mM sodium chloride, 0.02% sodium azide buffer adjusted to pH 7.4. These solutions were incubated, in the absence and presence of 500-μM of the aptamer consensus sequence, UUCACCG, at 37° C. and gently shaken at 100 rpm for 2 days. 40-4 of the reaction solution was then added to 500-4, of 5-μM Thioflavin T in 50-mM glycine/NaOH, pH 8.5. The fluorescence was read at excitation of 429 nm (2.5-nm slit) and emission of 489 nm (10-nm slit). 500-μM of the aptamer consensus sequence, UUCACCG, abolished amyloid aggregation.

FIGS. 3A-B show the direct binding of Aβ(1-40) peptide to cocaine. FIG. 3A shows a gel-shift binding assay using 20% native polyacrylamide gel in 89-mM Tris/89-mM boric acid/2-mM EDTA, pH 7.4. The gel was cast in a vertical electrophoresis system of dimensions 7×8×0.15 cm and run at 100 V for 2 hr at room temperature. Lane I contains 7-μM [$^3$H]-cocaine only and Lane II contains 7-μM [$^3$H]-cocaine and 125-μM Aβ(1-40) peptide. The gel was then phosphor imaged; the contrast of the image was enhanced using ImageJ 1.34, in the process of which the contrast of the band streaks compared to background was lost. The square boxes correspond to the free [$^3$H]-cocaine trapped in the well; the circle corresponds to the [$^3$H]-cocaine bound to Aβ(1-40). FIG. 3B shows the same gel as in FIG. 3A stained with Coomassie Brilliant Blue to indicate the position of the Aβ(1-40) peptide (circle). The position of the peptide corresponded to the [$^3$H]-cocaine bound to Aβ(1-40) (circle) in the phosphorimage in FIG. 3A.

Figure 4A:
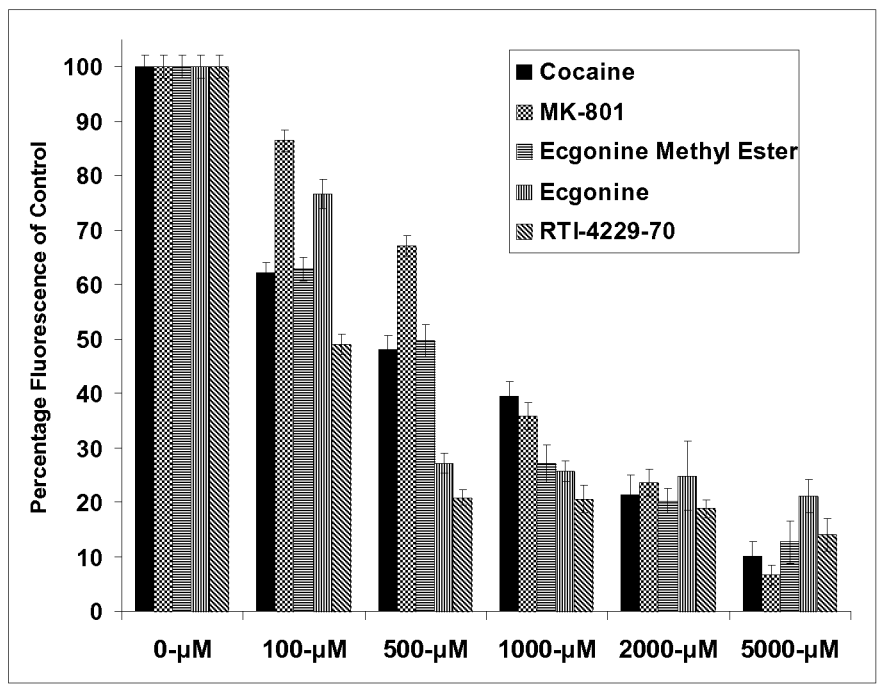
Figure 4B:
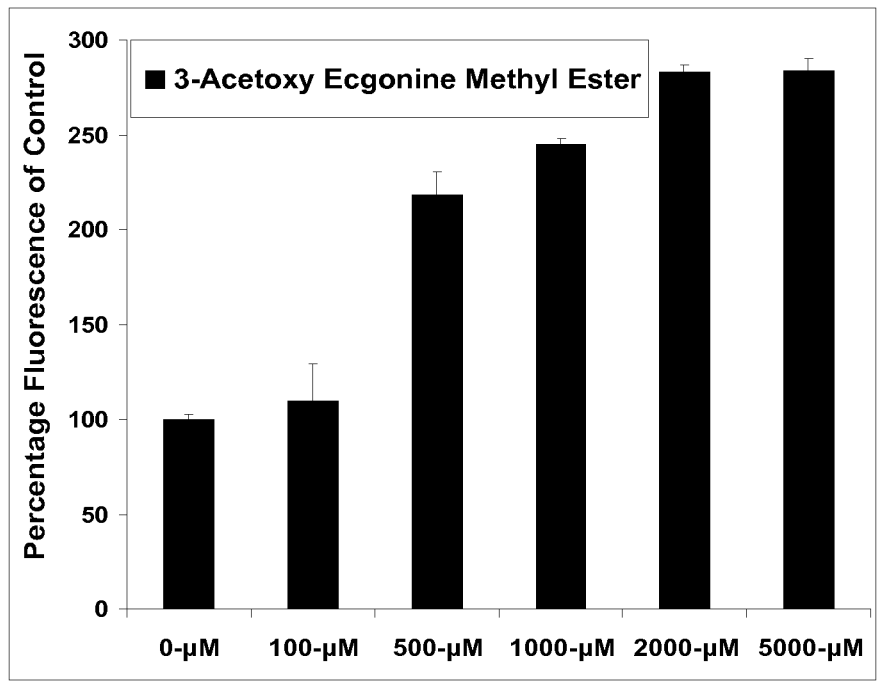

FIGS. 4A-B show the effect of cocaine, MK-801, and other compounds that alleviate cocaine inhibition of the nicotinic acetylcholine receptor on the aggregation of Aβ(1-40) peptides. 50-μM Aβ(1-40) solutions were made in 50-mM sodium phosphate, 100-mM sodium chloride, 0.02% sodium azide buffer adjusted to pH 7.4. These solutions were incubated, in the absence and presence of different concentrations of cocaine, MK-801, and some cocaine-alleviating ligands, at 37° C. and gently shaken at 100 rpm for 2 days. 10-μl of the reaction solution was then added to 500-μl of 5-μM Thioflavin T in 50-mM glycine/NaOH, pH 8.5. The fluorescence was read at excitation of 450 nm (3 nm slit) and emission of 482 nm (5 nm slit) using a Perkin-Elmer Model LS-5B Luminescence Spectrometer. FIG. 4A shows the dose-dependent inhibition of Aβ(1-40) peptide aggregation by cocaine, MK-801, ecgonine methyl ester, ecgonine, and RTI-4229-70. FIG. 4B shows the dose-dependent acceleration in Aβ(1-40) peptide aggregation by 3-acetoxy ecgonine methyl ester.

Figure 5:
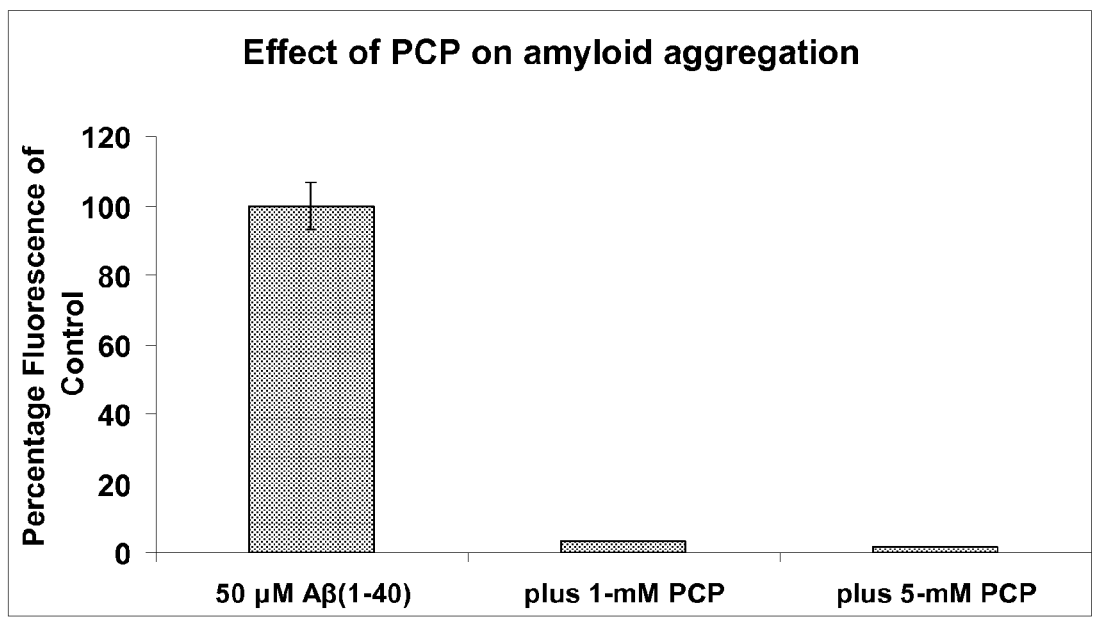

FIG. 5 shows inhibition of Aβ(1-40) peptide aggregation by phencyclidine (PCP). 50-μM Aβ(1-40) solutions were made in 50-mM sodium phosphate, 100-mM sodium chloride, 0.02% sodium azide buffer adjusted to pH 7.4. These solutions were incubated, in the absence and presence of 500-μM or 100-μM concentrations of PCP at 37° C. and gently shaken at 100 rpm for 2 days. 40-μl of the reaction solution was then added to 500-μl of 5-μM Thioflavin T in 50-mM glycine/NaOH, pH 8.5. The fluorescence was read at excitation of 429 nm (2.5 nm slit) and emission of 489 nm (10-nm slit). 1-mM PCP abolished amyloid aggregation.

DETAILED DESCRIPTION OF THE INVENTION

The present invention relates generally to the use of cocaine-binding-site ligands and/or cocaine-binding-site RNA aptamers (i) to treat or prevent Alzheimer's Disease in a subject and/or (ii) to reduce or prevent aggregation of beta-amyloid peptides in a subject. The present invention contemplates that any ligand or RNA aptamer that is able to bind to or interact with a cocaine-binding-site of the nicotinic acetylcholine receptor can also bind to, and interact with, the newly discovered cocaine-binding site on beta-amyloid peptide and be used in the methods described herein. As used herein, the term "beta-amyloid peptide" includes, but is not limited to, beta-amyloid peptide Aβ(1-40) and beta-amyloid peptide Aβ(1-42). The present invention also contemplates that any ligand or RNA aptamer that is able to bind to or interact with the cocaine-binding site of the nicotinic acetylcholine receptor can be used in the methods described herein.

In one aspect, the present invention relates to a method of treating or preventing Alzheimer's Disease in a subject by using a cocaine-binding-site ligand. This method involves administering to the subject a cocaine-binding-site ligand under conditions effective to treat or prevent Alzheimer's Disease in the subject. The cocaine-binding-site ligand used in this method is one that binds to a cocaine-binding site of a beta-amyloid peptide. Further details with respect to the cocaine-binding-site ligands used in this method are detailed herein below. Details regarding the steps and components of this method are also described in greater detail herein below.

In another aspect, the present invention relates to a method of reducing or preventing aggregation of beta-amyloid peptides in a subject by using a cocaine-binding-site ligand. This method involves administering to the subject a cocaine-binding-site ligand under conditions effective to reduce or prevent aggregation of beta-amyloid peptides in the subject. The cocaine-binding-site ligand used in this method is one that binds to a cocaine-binding site of a beta-amyloid peptide. Further details with respect to the cocaine-binding-site ligands used in this method are detailed herein below. Details regarding the steps and components of this method are also described in greater detail herein below.

In one embodiment, the cocaine-binding-site ligand used in this method is one that binds to a cocaine-binding site of a beta-amyloid peptide or to the cocaine-binding site of the nicotinic acetylcholine receptor that has a functional motif similar to the cocaine-binding site of the beta-amyloid peptide. Some of the cocaine-binding-site ligands are known not to be toxic.

According to one embodiment, the cocaine-binding-site ligand used in the methods of the present invention can include an organic compound that is a derivative or analogue of tropane. The general chemical structures of tropane derivatives are as follows:

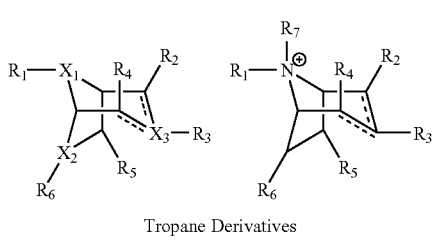

Tropane Derivatives where $R_1$, $R_2$, $R_3$, $R_4$, $R_5$, $R_6$, and $R_7$ are the same or different and are independently selected from the group consisting of hydrogen, hydroxyl, alkyl, cycloalkyl, alkenyl, alkoxy, aryl, alkylaryl, isoxazole, thiophene, indol, naphthalene, heterocyclic ring, halogen, and amine, as well as their esters and ethers, and $X_1$, $X_2$, and $X_3$ are independently selected from the group consisting of N, S, O, and C.

A preferred tropane derivative of the present invention is the organic compound commonly referred to as cocaine. As referred to herein, the chemical structure of cocaine is as follows:

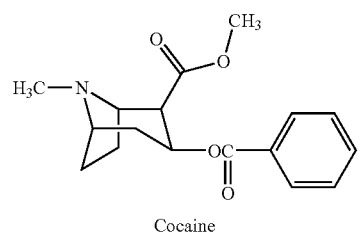

Cocaine

Additional cocaine-binding-site ligands that are derivatives of cocaine, and are suitable for use in the methods of the present invention, include, but are not limited to, the following organic compounds: ecgonine; ecgonine methyl ester; RTI-4229-70; RCS-III-143; RCS-III-140A; RCS-III-218; RCS-III-202A; and metabolites, analogues, and/or derivatives of these compounds.

As referred to herein, the organic compound "ecgonine" has the following chemical structure:

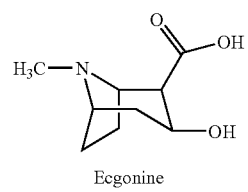

Ecgonine

As referred to herein, the organic compound "ecgonine methyl ester" has the following chemical structure:

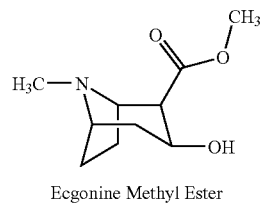

Ecgonine Methyl Ester

As referred to herein, the organic compound "RTI-4229-70" has the following chemical structure:

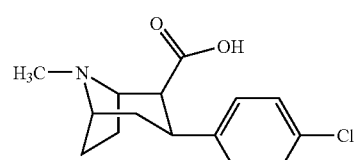

RTI-4229-70

As referred to herein, the organic compound "RCS-III-143" has the following chemical structure:

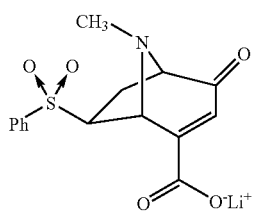

RCS-III-143

As referred to herein, the organic compound "RCS-III-140A" has the following chemical structure:

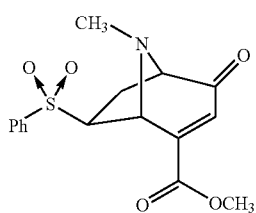

RCS-III-140A

As referred to herein, the organic compound "RCS-III-218" has the following chemical structure:

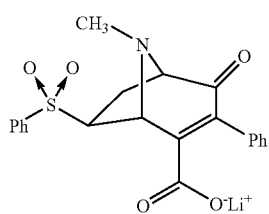

RCS-III-218

As referred to herein, the organic compound "RCS-III-202A" has the following chemical structure:

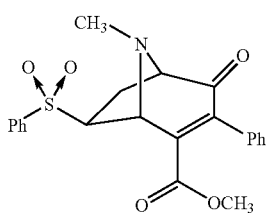

RCS-III-202A

In another embodiment, the cocaine-binding-site ligand used in the methods of the present invention can include one of the following cocaine analogues and derivatives:

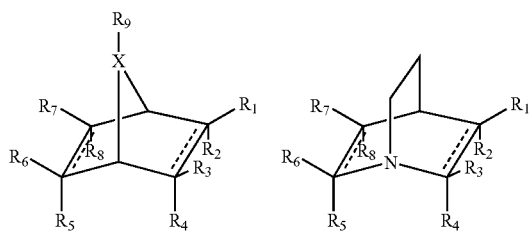

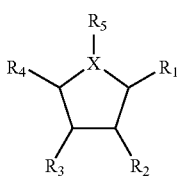

where $R_1$, $R_2$, $R_3$, $R_4$, $R_5$, $R_6$, $R_7$, $R_8$, and $R_9$ are the same or different and are independently selected from the group consisting of hydrogen, hydroxyl, alkyl, cycloalkyl, alkenyl, alkoxy, aryl, alkylaryl, isoxazole, thiophene, indol, naphthalene, heterocyclic ring, halogen, and amine, as well as their esters and ethers, and X is independently selected from the group consisting of N, S, O, and C.

In another embodiment, the cocaine-binding-site ligand used in the methods of the present invention can include derivatives or analogues of piperidine. As referred to herein, the general chemical structure of piperidine derivatives is as follows:

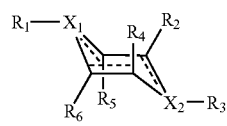

Piperidine Derivatives where $R_1$, $R_2$, $R_3$, $R_4$, $R_5$, and $R_6$ are the same or different and are independently selected from the group consisting of hydrogen, hydroxyl, alkyl, cycloalkyl, alkenyl, alkoxy, aryl, alkylaryl, isoxazole, thiophene, indol, naphthalene, heterocyclic ring, halogen, and amine, as well as their esters and ethers, and $X_1$ and $X_2$ are independently selected from the group consisting of N, S, O, and C.

In another embodiment, the cocaine-binding-site ligand used in the methods of the present invention is dizocilpine, also known as MK-801, and derivatives or analogues thereof. As referred to herein, the general chemical structures of MK-801 derivatives are as follows:

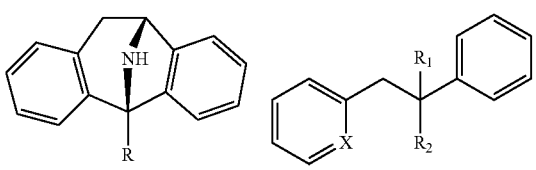

MK-801 Derivatives where R, $R_1$, and $R_2$ are the same or different and are independently selected from the group consisting of hydrogen, hydroxyl, alkyl, cycloalkyl, alkenyl, alkoxy, aryl, alkylaryl, halogen, and amine, as well as their esters and ethers, and X is N or C.

In another embodiment, the cocaine-binding-site ligand used in the methods of the present invention can include phencyclidine (PCP) and derivative or analogues thereof. As referred to herein, the chemical structure of the PCP derivatives is as follows:

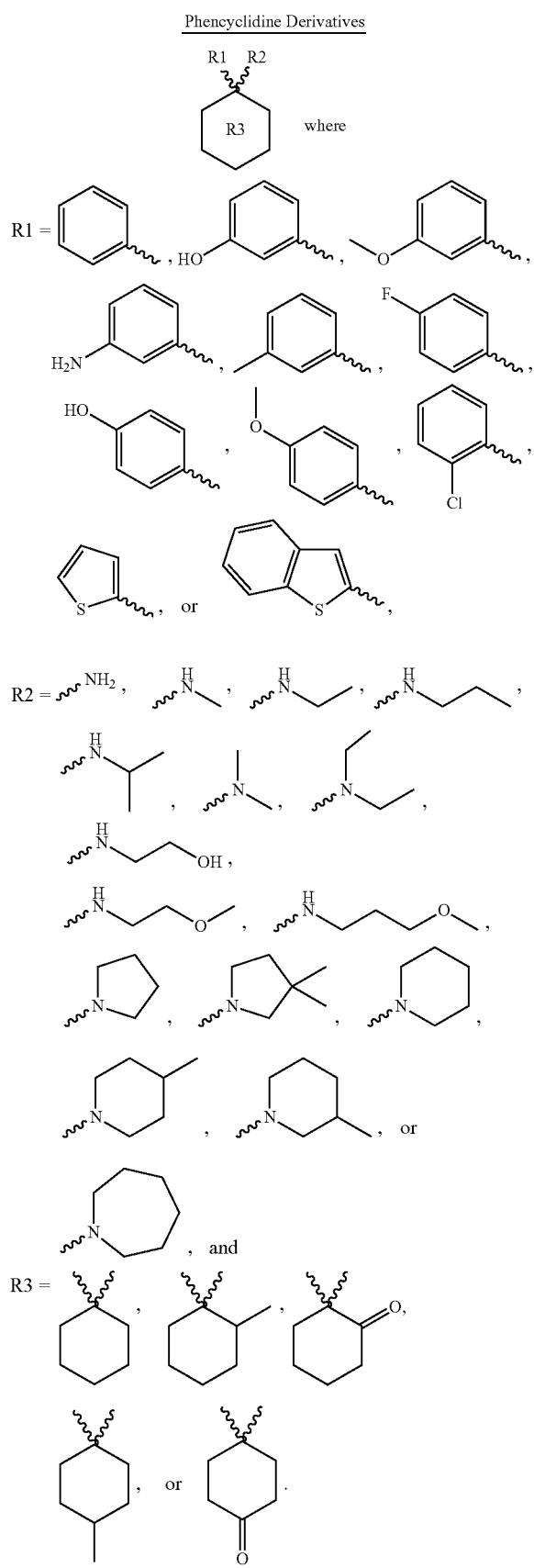

In another aspect, the present invention relates to a method of treating or preventing Alzheimer's Disease in a subject by using a cocaine-binding-site RNA aptamer. This method involves administering to the subject a cocaine-binding-site RNA aptamer under conditions effective to treat or prevent Alzheimer's Disease in the subject. The RNA aptamer used in this method is one that binds to a cocaine-binding site of a beta-amyloid peptide. Further details with respect to the cocaine-binding-site RNA aptamers used in this method are detailed herein below. Details regarding the steps and components of this method are also described in greater detail herein below.

Yet another aspect of the present invention relates to a method of reducing or preventing aggregation of beta-amyloid peptides in a subject by using a cocaine-binding-site RNA aptamer. This method involves administering to the subject a cocaine-binding-site RNA aptamer under conditions effective to reduce or prevent aggregation of beta-amyloid peptides in the subject. The RNA aptamer used in this method is one that binds to a cocaine-binding site of a beta-amyloid peptide. Further details with respect to the cocaine-binding-site RNA aptamers used in this method are detailed herein below. Details regarding the steps and components of this method are also described in greater detail herein below.

According to one embodiment, the cocaine-binding-site RNA aptamers used in the methods of the present invention can include any RNA aptamer that is able to bind to a cocaine-binding site of a beta-amyloid peptide.

Suitable examples of RNA aptamers that can be used in the methods of the present invention, include, but are not limited to, RNA aptamers having a consensus sequence according to:

| | | |
|---|---|---|
| (a) | SEQ ID NO: 1 | (i.e., ACCG), |
| | SEQ ID NO: 2 | (i.e., UCCG), |
| | SEQ ID NO: 3 | (i.e., UUUACCG), |
| | SEQ ID NO: 4 | (i.e., UUCACCG), |
| and/or | | |
| | SEQ ID NO: 5 | (i.e., UUCACCGUAAGG); |
| (b) | SEQ ID NO: 6 | (i.e., AUCACCGUAAGG (see Aptamer B5)), |
| | SEQ ID NO: 7 | (i.e., UUUACCGUAAGG (see Aptamer B15)), |
| | SEQ ID NO: 8 | (i.e., UUUUCCGUAAGG (see Aptamer B19)), |
| | SEQ ID NO: 9 | (i.e., UUUACCGUAAGG (see Aptamer B27)), |
| | SEQ ID NO: 10 | (i.e., AUCACCGUAAGG (see Aptamer B28)), |
| | SEQ ID NO: 11 | (i.e., UCCACCGUAGAU (see Aptamer B36)), |
| | SEQ ID NO: 12 | (i.e., AUCACCGUAAGG (see Aptamer B44)), |
| | SEQ ID NO: 13 | (i.e., UUUACCGUAAGG (see Aptamer B55)), |
| | SEQ ID NO: 14 | (i.e., UCCACCGUAAGA (see Aptamer B59)), |
| | SEQ ID NO: 15 | (i.e., UCCACCGUAAGA (see Aptamer B61)), |

```
            -continued
SEQ ID NO: 16    (i.e., UUUACCGUAAGG
                 (see Aptamer B64)), SEQ ID NO: 17    (i.e., UUUACCGUAAGG
                 (see Aptamer B65)), SEQ ID NO: 18    (i.e., UUUACCGUAAGG
                 (see Aptamer B69)), SEQ ID NO: 19    (i.e., UCCACCGUAAGA
                 (see Aptamer B76)), SEQ ID NO: 20    (i.e., UUUUCCGUAAGG
                 (see Aptamer B78)), SEQ ID NO: 21    (i.e., UCCACCGUAAGA
                 (see Aptamer B108)), SEQ ID NO: 22    (i.e., UUUACCGUAAGG
                 (see Aptamer B111)),
and/or SEQ ID NO: 23    (i.e., AUCACCGUAAGG
                 (see Aptamer B124));

(c)  SEQ ID NO: 55    (i.e., GCUGAA);

(d)  SEQ ID NO: 66    (i.e., GAAAG);
and/or (e)  SEQ ID NO: 88    (i.e., GUUAAU).
```

More particularly, suitable examples of RNA aptamers that can be used in the methods of the present invention, include, but are not limited to, RNA aptamers having a nucleotide sequence according to:

(a) SEQ ID NO:24 (Aptamer B5), SEQ ID NO:25 (Aptamer B15), SEQ ID NO:26 (Aptamer B19), SEQ ID NO:27 (Aptamer B27), SEQ ID NO:28 (Aptamer B28), SEQ ID NO:29 (Aptamer B36), SEQ ID NO:30 (Aptamer B44), SEQ ID NO:31 (Aptamer B55), SEQ ID NO:32 (Aptamer B59), SEQ ID NO:33 (Aptamer B61), SEQ ID NO:34 (Aptamer B64), SEQ ID NO:35 (Aptamer B65), SEQ ID NO:36 (Aptamer B69), SEQ ID NO:37 (Aptamer B76), SEQ ID NO:38 (Aptamer B78), SEQ ID NO:39 (Aptamer B108), SEQ ID NO:40 (Aptamer B111), and/or SEQ ID NO:41 (Aptamer B124);

(b) SEQ ID NO:42 (Aptamer 01), SEQ ID NO:43 (Aptamer 05), SEQ ID NO:44 (Aptamer 06), SEQ ID NO:45 (Aptamer 07), SEQ ID NO:46 (Aptamer 09), SEQ ID NO:47 (Aptamer 11), SEQ ID NO:48 (Aptamer 13), SEQ ID NO:49 (Aptamer 14), SEQ ID NO:50 (Aptamer 16), SEQ ID NO:51 (Aptamer 18), SEQ ID NO:52 (Aptamer 19), SEQ ID NO:53 (Aptamer 20,21), and/or SEQ ID NO:54 (Aptamer 22);

(c) SEQ ID NO:56 (Aptamer 3), SEQ ID NO:57 (Aptamer 8), SEQ ID NO:58 (Aptamer 23), SEQ ID NO:59 (Aptamer 24), SEQ ID NO:60 (Aptamer 26), SEQ ID NO:61 (Aptamer 30), SEQ ID NO:62 (Aptamer 31), SEQ ID NO:63 (Aptamer 38), SEQ ID NO:64 (Aptamer 39), and/or SEQ ID NO:65 (Aptamer 42);

(d) SEQ ID NO:67 (Aptamer S1), SEQ ID NO:68 (Aptamer S13), SEQ ID NO:69 (Aptamer S14), SEQ ID NO:70 (Aptamer S21), SEQ ID NO:71 (Aptamer S24), SEQ ID NO:72 (Aptamer S29), SEQ ID NO:73 (Aptamer S43), SEQ ID NO:74 (Aptamer S44), SEQ ID NO:75 (Aptamer S45), SEQ ID NO:76 (Aptamer S46), SEQ ID NO:77 (Aptamer S47), SEQ ID NO:78 (Aptamer S49), SEQ ID NO:79 (Aptamer S50), SEQ ID NO:80 (Aptamer S53), SEQ ID NO:81 (Aptamer S56), SEQ ID NO:82 (Aptamer S59), SEQ ID NO:83 (Aptamer S62), SEQ ID NO:84 (Aptamer S15), SEQ ID NO:85 (Aptamer S17), SEQ ID NO:86 (Aptamer S28), and/or SEQ ID NO:87 (Aptamer S54); and/or (e) SEQ ID NO:89 (Aptamer S5), SEQ ID NO:90 (Aptamer S18), SEQ ID NO:91 (Aptamer S20), SEQ ID NO:92 (Aptamer S25), SEQ ID NO:93 (Aptamer S48), SEQ ID NO:94 (Aptamer S51), and/or SEQ ID NO:95 (Aptamer S57).

The RNA aptamers used in the methods of the present invention can be chemically modified. A suitable method of doing this is by attaching a modifier to the RNA aptamer. Suitable examples of modifiers can include, without limitation, fluoro modifiers and methoxy modifiers, as well as other RNA aptamer modifiers well known by those of ordinary skill in the relevant art.

The sequences (consensus and RNA aptamer nucleotide sequences) referenced above by "SEQ ID NO." are identified herein below in Tables A, B, C, D, E, and F.

TABLE A

Consensus Regions of Selected RNA Aptamers

| RELATED APTAMER | CONSENSUS REGION | SEQ ID NO: |
|---|---|---|
| Consensus | ACCG | 1 |
| Consensus | UCCG | 2 |
| Consensus | UUUACCG | 3 |
| Consensus | UUCACCG | 4 |
| Consensus | UUCACCGUAAGG | 5 |
| B5 | AUCACCGUAAGG | 6 |
| B15 | UUUACCGUAAGG | 7 |
| B19 | UUUUCCGUAAGG | 8 |
| B27 | UUUACCGUAAGG | 9 |
| B28 | AUCACCGUAAGG | 10 |
| B36 | UCCACCGUAGAU | 11 |
| B44 | AUCACCGUAAGG | 12 |
| B55 | UUUACCGUAAGG | 13 |
| B59 | UCCACCGUAAGA | 14 |
| B61 | UCCACCGUAAGA | 15 |
| B64 | UUUACCGUAAGG | 16 |
| B65 | UUUACCGUAAGG | 17 |
| B69 | UUUACCGUAAGG | 18 |
| B76 | UCCACCGUAAGA | 19 |
| B78 | UUUUCCGUAAGG | 20 |
| B108 | UCCACCGUAAGA | 21 |
| B111 | UUUACCGUAAGG | 22 |
| B124 | AUCACCGUAAGG | 23 |

TABLE B

Selected RNA Aptamer Sequences

| APTAMER | SEQUENCE | SEQ ID NO: |
|---|---|---|
| B5 | 5'-CUCGAUCACCGUAAGGACAUCUACGUAAGUGUAAUGCGGCUUGUUUUCCCCAUGCGUCUGCAUAUCUGUU-3' | 24 |
| B15 | 5'-UUUACCGUAAGGCCUGUCAUCGUUUGACAGCGGCUUGUUGACCCUUCCACUAUGUGUGCCUGUAAUG-3' | 25 |
| B19 | 5'-ACUUCGUCUUGCAGCGCGGCUUGUCUCUUCCCACAUCCGUUCUAUCGGUAUGACUCUUUUUCCGUAAGGUCA-3' | 26 |
| B27 | 5'-UUUACCGUAAGGCCUGUCUUCGUUUGACAGCGGCUUGUUGACCCUCACACUUUGUACCUCUGCCUG-3' | 27 |
| B28 | 5'-CUCGAUCACCGUAAGGACAUCUACAUAAGUGUAAUGCGGCUUGUUUUCCCCAUGCAUCUGCAUAUCUGU-3' | 28 |
| B36 | 5'-UGUCCACCGUAGAUUGUAAACUAUCGCGUAAAGCGAAGUUUAUGUGGCUUGUUUCCCACGCCUUG-3' | 29 |
| B44 | 5'-CUCGAUCACCGUAAGGACAUUUACGUAAGUGUAAUGCGGCUUGUUUUCCCCAUGCGUCUGCAUAUCUGU-3' | 30 |
| B55 | 5'-UUUACCGUAAGGCCUGUCUUCGUUUGACAGCGGCUUGUUGACCCUCACACUUUGUACCUGCUGCCAA-3' | 31 |
| B59 | 5'-UCCACCGUAAGAUUGUAAACUAUCGGGUAAAGACGAAGUUUAUGUGGCUUGUUUCCCACCGCCUUGCC-3' | 32 |
| B61 | 5'-UGUCCACCGUAAGAUUGUAAACUAUCGUAAAGACGAAGUUUAUGUGGCUUGUUUCCCACCGCCUUGCC-3' | 33 |
| B64 | 5'-UUUACCGUAAGGCCUGUCAUCGUUUGACAGCGGCUUGUUGACCCUUCCACUAUGUGUGCCUGUAAUG-3' | 34 |
| B65 | 5'-UUUACCGUAAGGCCUGUCUUCGUUUGACAGCGGCUUGUUGACCCACACACUUUGUCCCGGCUGCAG-3' | 35 |
| B69 | 5'-UUUACCGUAAGGCCUGUCUUCUUUUGACAGCGGCUUGUUGACCCUCACGCUUUGUCCCUGCUGUACCUG-3' | 36 |
| B76 | 5'-UCCACCGUAAGAUUGUAAACUAUCGCGUAAAAGACGAAGUUUAUGUGGCUUGUUUCCCACCGCCUUG-3' | 37 |
| B78 | 5'-ACUUCGUCUUGCAGCGCGGCUUGUCUUCCCACAUCCGUUCUAUCGGUAUGACUUUUUCCGUAAGGUCA-3' | 38 |
| B108 | 5'-UCCACCGUAAGAUUGUAAACUAUCGCGUAAAGACGAAGUUUAUGUGGCUUGUUUCCCACCACCUUGCG-3' | 39 |
| B111 | 5'-UUUACCGUAAGGCCUGUCUUCGUUUUGACAGCGGCUUGUUGACCCUCACGCUUUGUCCCAUGCCCGUC-3' | 40 |
| B124 | 5'-CUCGAUCACCGUAAGGACAUUUACGUAAGUGUAAUGCGGCUUGUUUUCCCCAUGCGUUUGCAUAUCUGUG-3' | 41 |

TABLE C

Sequences of Selected RNA Aptamers that Inhibit the Nicotinic Acetylcholine Receptor by Binding to the Cocaine Site on the Receptor

| APTAMER | SEQUENCE | SEQ ID NO: |
|---|---|---|
| 01 | ACGUUGAGUACAACCCCACCCCGUUCACGGUAGCCCUGUA | 42 |
| 05 | GCUACAGUACAACGGGCCGUGUGGAAUACACCGACAAGG | 43 |
| 06 | UCCACCGAUCUAGAUGAUCCAGGCACCCGACCACCACCUC | 44 |
| 07 | GCUUGUGGACCAAGAAGCAACCAGUCACCGUUGCCCC | 45 |
| 09 | CAACAGUCCUGUGUCCGUUGAAUCCUCUAGAUCCAGGGUG | 46 |

TABLE C-continued

Sequences of Selected RNA Aptamers that Inhibit the
Nicotinic Acetylcholine Receptor by Binding to the
Cocaine Site on the Receptor

| APTAMER | SEQUENCE | SEQ ID NO: |
|---|---|---|
| 11 | GGACCCCCACAGCAAGUUUGCCGGCGACCGCGUUCUUG | 47 |
| 13 | CUUGCCACUCCUGUCUAGCUGGCGUAGACCGCGCAGAAAG | 48 |
| 14 | GCUAGUAGCCUCAGCAGCAUAGUUUCGCCGCUAUGCAGUA | 49 |
| 16 | UAGCAUAAUGUGGAGCGUUGACCGGACCUCUCCAGUCGUA | 50 |
| 18 | UGGACUACGCACCCGCUAGUCCGUCCAAGAACUGUGCG | 51 |
| 19 | UUCUGUUCCGACCAAUUGAAUAGUCACCGUGAUGAUUUGA | 52 |
| 20, 21 | GAUGCCAGCGCGCAUUCUUCACCGAAGUACGUAUCCACG | 53 |
| 22 | UUCGCCGCUGCACUCUCGCAGCACUGGUCGGGAUGUGUC | 54 |

TABLE D

Sequences of RNA Aptamers that Alleviate Cocaine Inhibition
of the Nicotinic Acetylcholine Receptor

| APTAMER | SEQUENCE | SEQ ID NO: |
|---|---|---|
| Consensus | GCUGAA | 55 |
| 3 | AGUAGGAAUACCCCCAUCCAAAGCUCGCUAGGCUGAACAC | 56 |
| 8 | GACGGCCCGAGAUUGCAGAAAAACGCGCCCACGUGUCAGA | 57 |
| 23 | UCCCUAGCUGACGAUGGAUCUUGGAUCACAUAGGCUGCGC | 58 |
| 24 | GGACAUGCCGGUCUUGAGCGGAGGUGAACCGUACCACG | 59 |
| 26 | AACACGCCUCAGGACGCCAGGUGAACCCUCGAACC | 60 |
| 30 | AACGCUGAAUCCCCCGGUCAUAGAACUUUGAUAGUACAG | 61 |
| 31 | UACUGAAUGAUCUCCACCCGCCGGAAUGCGUAUAGUCCCU | 62 |
| 38 | GCUGGGGAAAGCAGGUCCGUUCCCACCGCCUGAAGCUUUG | 63 |
| 39 | CCUCCUGACACAACCACCCAACCACCUUCUUGAAACAUUU | 64 |
| 42 | ACAACCUUGAUUGCUUGAAACCUCUAACCCGAGGCUCUGUA | 65 |

TABLE E

Sequences of 2'-Fluoropyrimidine-Modified RNA Aptamers that
Inhibit the Nicotinic Acetylcholine Receptor by Binding to the
Cocaine Site on the Receptor

| APTAMER | SEQUENCE | SEQ ID NO: |
|---|---|---|
| Consensus | GAAAG | 66 |
| S1 | CGAACGUGGACGAAGGGCGGUUUGUGAGUGCUUA | 67 |
| S13 | CUGACUGCGUCUCUAUAUGACAUAGGCGAUGAGAAAGCAGA | 68 |
| S14 | GGAACAGACGUCAUCUGUGGCACGUCCGCUGCUAGCAGAGA | 69 |
| S21 | GACACAAGCUGGACCACGUCAAGCGUUUUGUGAAAGCAGGU | 70 |
| S24 | UGGCAUCUUGUGCAUGACAACAGAGGGUGAAACCAACGGGU | 71 |

TABLE E-continued

Sequences of 2'-Fluoropyrimidine-Modified RNA Aptamers that Inhibit the Nicotinic Acetylcholine Receptor by Binding to the Cocaine Site on the Receptor

| APTAMER | SEQUENCE | SEQ ID NO: |
|---|---|---|
| S29 | AAACUUGCCUUGGUUUAUAACGUAACAAUACAGAACGA | 72 |
| S43 | AGAAUCUAAGACGUGAAAAUGGUAAGACAUUCUCUACC | 73 |
| S44 | AGGUGUGCGCAGACGAAUAGGGUUGUGCGAAAGUCUAGCA | 74 |
| S45 | UUUAGAGUUGAAAUGCGUAAUGGUUAAAUGAUCCAUUCUG | 75 |
| S46 | AACAAUGCGAGGGUAAAAGCAUGUUCUAACCAGGGAGGGA | 76 |
| S47 | AUGGAAGCCCUUGAUUCUACGGAUCUAGCGAGAUUU | 77 |
| S49 | CCUGUAAGGGCGAAACUAAGCGAGAAAUCAUUAGGAUGA | 78 |
| S50 | CUCAAUGCAUACGCUGGUCAACGGGACGAUUAGUGACAAGGCCGC | 79 |
| S53 | AAUAAGUGGCAAGUAGCCUAGAGAUUAGAAGACCUCAAC | 80 |
| S56 | AAUUGACGAGCUGGUGGGAGAUAGUCUCAGGUAUCUUGUGC | 81 |
| S59 | GGUGGACAGUAACUCCUUGAUGCGGUAGAUUCGUAGC | 82 |
| S62 | UACGCGCUUAUGAUAAAGGGUUAGAAGGACGAGCGUCGCA | 83 |
| S15 | CACAUGCAGAGUAGUGUAAGGUAACACCCAGGUUUUUUG | 84 |
| S17 | CCGGGGCGCAGGUGUCCCUGACGAUGAUCAAUUUCGGGUGA | 85 |
| S28 | GACGCCUUUAUGAAUGACCAGGGAAGUUGUCAGAAGAGG | 86 |
| S54 | GUCACUUUCUGAAUGGGAGAUAUCUUCGAUAUGGUAAU | 87 |

TABLE F

Sequences of 2'-Fluoropyrimidine-Modifled RNA Aptamers that Alleviate Cocaine Inhibition of the Nicotinic Acetylcholine Receptor

| APTAMER | SEQUENCE | SEQ ID NO: |
|---|---|---|
| Consensus | GUUAAU | 88 |
| S5 | GAAGGCGAAAGGCACAAAGAUCUGAUGAAGUUAAUGGAUCA | 89 |
| S18 | GUUAAUCGCUGAAUAUUCGAAGUGCUUUCCGUGAU | 90 |
| S20 | UGGGCUUAGGUGUUAAGUCGAUGACUGUUCAUUCUCGGUA | 91 |
| S25 | ACGUGAGCGAGCAAUAAAAGUCCCCUGGGGCGGAGUUAAA | 92 |
| S48 | GGGAGAGUCUACGGAUCCUAGAAAAAGCAGGACGUUAUU | 93 |
| S51 | CAAAGGGGAGCCACGGGGCGACGUGUAAUCCUCUAUUCAGCA | 94 |
| S57 | AAUGAAGGCAAUUCUUUAACGUUAAUAGGAAGGGGUAAA | 95 |

RNA aptamers are preferred types of nucleic acid elements that have affinity to and can bind to a target molecule. Aptamers typically are generated and identified from a combinatorial library (typically in vitro) wherein a target molecule, generally although not exclusively a protein or nucleic acid, is used to select from a combinatorial pool of molecules, generally although not exclusively oligonucleotides, those that are capable of binding to the target molecule. The selected reagents can be identified as primary aptamers. The term "aptamer" includes not only the primary aptamer in its original form, but also secondary aptamers derived from (i.e., created by minimizing and/or modifying the structure of) the primary aptamer. Aptamers, therefore, behave as ligands, binding to their target molecule.

Identifying primary aptamers basically involves selecting aptamers that bind a target molecule with sufficiently high affinity (e.g., $K_d$=20-50 nM) and specificity from a pool of nucleic acids containing a random region of varying or predetermined length (Shi et al., "A Specific RNA Hairpin Loop Structure Binds the RNA Recognition Motifs of the *Droso-*

*phila* SR Protein B52," *Mol. Cell. Biol.* 17:1649-1657 (1997), which is hereby incorporated by reference in its entirety).

To identify primary aptamers of any particular target molecule, an established in vitro selection and amplification scheme, SELEX, can be used. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk and Gold, "Systematic Evolution of Ligands by Exponential Enrichment: RNA Ligands to Bacteriophage T4 DNA Polymerase," *Science* 249:505-510 (1990), which are hereby incorporated by reference in their entirety.

In the case of RNA aptamers, where the structure and sequence of the RNA has been established, the RNA molecule can either be prepared synthetically or a DNA construct or an engineered gene capable of encoding such an RNA molecule can be prepared. Therefore, another aspect of the present invention relates to a DNA molecule and, more particularly, an engineered gene which encodes an RNA aptamer of the present invention.

An engineered gene of the present invention includes a DNA sequence encoding an RNA aptamer (also referred to herein as an "RNA molecule") of the present invention, which DNA sequence is operably coupled to 5' and/or 3' regulatory regions as needed to ensure proper transcription of the RNA aptamer in host systems.

Transcription of the DNA molecule of the present invention is dependent upon the presence of a promoter, which is a DNA sequence that directs the binding of RNA polymerase and thereby promotes RNA synthesis. The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). For the purposes of expressing the constructed DNA molecule or engineered gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV 5, ompF, bla, lpp, and the like, may be used to direct high levels of transcription of adjacent DNA segments. Additionally, a hybrid trp-lacUV 5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the DNA sequence encoding the RNA molecule. Depending upon the desired activity, it is possible to select the promoter for not only in vitro production of the RNA molecule of the present invention, but also in vivo production in cultured cells or whole organisms, as described below. Because in vivo production can be regulated genetically, a preferable type of promoter is an inducible promoter which induces transcription of the DNA sequence in response to specific conditions, thereby enabling expression of the RNA molecule according to desired therapeutic needs (i.e., expression within specific tissues, or at specific temporal and/or developmental stages).

Preferred promoters for use in the engineered gene of the present invention include a T7 promoter, a SUP4 tRNA promoter, an RPR1 promoter, a GPD promoter, a GAL1 promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the RNA molecules of the present invention (Milligan et al., "Oligoribonucleotide Synthesis Using T7 RNA Polymerase and Synthetic DNA Templates," *Nucleic Acids Res.* 15(21):8783-8798 (1987), which is hereby incorporated by reference in its entirety). The SUP4 tRNA promoter and RPR1 promoter are driven by RNA polymerase III of the yeast *Saccharomyces cerevisiae*, and suitable for high level expression of RNA less than 400 nucleotides in length (Kurjan et al., Mutation at the Yeast SUP4 tRNA$^{tyr}$ Locus: DNA Sequence Changes in Mutants Lacking Supressor Activity," *Cell* 20:701-709 (1980) and Lee et al., "Expression of RNase P RNA in *Saccharomyces cerevisiae* is Controlled by an Unusual RNA Polymerase III Promoter," *Proc. Natl. Acad. Sci. USA* 88:6986-6990 (1991), which are hereby incorporated by reference in their entirety). The glyceraldehydes-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," *Gene* 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10. Promoter in *Saccharomyces cerevisiae*," *Mol. Cell. Biol.* 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. The heat shock promoter used in the present invention can be a *Drosophila* hsp70 promoter, more preferably a portion of the *Drosophila* hsp70 promoter which is fully functional with regard to heat inducibility and designated heat inducible cassette, or Hic (Kraus et al., "Sex-Specific Control of *Drosophila melanogaster* Yolk Protein 1 Gene Expression is Limited to Transcription," *Mol. Cell. Biol.* 8:4756-4764 (1988), which is hereby incorporated by reference in its entirety). Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety). An additional promoter used in the present invention is a constructed hybrid promoter in which the yeast upstream activation sequence for the GAL1 genes was fused to the core *Drosophila* hsp70 promoter (Brand and Perrimon, "Targeted Gene Expression as a Means of Altering Cell Fates and Generating Dominant Phenotypes," *Development* 118:401-415 (1993), which is hereby incorporated by reference in its entirety). This promoter is no longer activated by heat shock. Rather, it is activated by the yeast GAL4 protein, a transcription activator that is normally not present in *Drosophila*. The yeast GAL4 gene has been introduced into *Drosophila*, and is itself under a variety of transcriptional control in different fly lines.

Initiation of transcription in mammalian cells requires a suitable promoter, which may include, without limitation, β-globin, GAPDH, β-actin, actin, Cstf2t, SV40, MMTV, metallothionine-1, adenovirus E1a, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the RNA molecules of the present invention, providing a means to restrict the expression of the RNA molecules in particular tissues.

For gene expression in plant cells, suitable promoters may include, without limitation, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself. See C. E. Vallejos, et al., "Localization in the Tomato Genome of DNA Restriction Fragments Containing Sequences Homologous to the rRNA (45S), the major chlorophyll A/B Binding Polypeptide and the Ribulose Bisphosphate Carboxylase Genes," *Genetics* 112: 93-105 (1986), which is hereby incorporated by reference in its entirety, and discloses the small subunit materials. The nos promoter and the 35S promoter of cauliflower mosaic virus are well known in the art.

In addition, the engineered gene may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley et al., "Expression of Bacterial Genes in Plant Cells," *Proc. Nat'l. Acad. Sci. USA,* 80:4803-4807 (1983), which is hereby incorporated by reference in its entirety) and the cauliflower mosaic virus 3' regulatory region (Odell et al., "Identification of DNA Sequences Required for Activity of the Cauliflower Mosaic Virus 35S Promoter," *Nature,* 313(6005):810-812 (1985), which is hereby incorporated by reference in its entirety). Virtually any 3' regulatory region known to be operable in plants would suffice for proper expression of the coding sequence of the engineered gene of the present invention.

To obtain high level expression of the RNA molecules (i.e., the RNA aptamers) of the present invention, the constructed DNA molecule or engineered gene can contain a plurality of monomeric DNA sequences ligated "head-to-tail," each of which encodes an RNA molecule of the present invention. This is particularly useful for augmenting the number of RNA molecules produced during each transcriptional event. By plurality, it is intended that the number of monomeric DNA sequences be at least two, preferably at least four, more preferably at least eight, and most preferably at least twelve. Such tandemly arrayed sequences are known to be relatively stable in bacteria (Lindquist, "Varying Patterns of Protein Synthesis in *Drosophila* During Heat Shock: Implications for Regulation," *Dev. Biol.* 77:463-479 (1980), which is hereby incorporated by reference in its entirety) and can persist for many generations in transgenic fly lines (Xiao and L is, "A consensus Sequence Polymer Inhibits In Vivo Expression of Heat Shock Genes," *Mol Cell Biol* 6:3200-3206 (1986); Shopland and L is, "HSF Recruitment and Loss at Most *Drosophila* Heat Shock Loci is Coordinated and Depends on Proximal Promoter Sequences," *Chromosoma* 105:158-171 (1996), which are hereby incorporated by reference in their entirety). This strategy should be applicable to other organisms. For example, long direct repeating sequences have been used in yeast (Robinett et al., "In Vivo Localization of DNA Sequences and Visualization of Largescale Chromatin Organization Using lac Operator/Repressor Recognition," *J. Cell Biol.* 135:1685-700 (1996), which is hereby incorporated by reference in its entirety). It should be apparent to those of ordinary skill in the art, however, that the number of monomeric DNA sequences can vary for each application of the DNA molecule.

Depending upon the desired application and intended use for the DNA molecule, it is possible to produce homopolymers containing a plurality of substantially identical monomeric DNA sequences or copolymers containing a plurality of substantially different monomeric DNA sequences. It is also possible to produce copolymers, block polymers, or combinations thereof, that contain a plurality of substantially different monomeric DNA sequences. The RNA molecules produced from such a homopolymer are a single type. In contrast, the RNA molecules produced from such a copolymer, a block polymer, or a combination thereof, are different types. Thus, the plurality of monomeric DNA sequences can be substantially identical (i.e., producing substantially the same RNA molecule) or they can be substantially different (i.e., producing substantially different RNA molecules). When the plurality of monomeric DNA sequences are substantially different, the resulting RNA molecules can be directed to the same or to different target molecules.

When the DNA molecule encodes a plurality of monomeric DNA sequences, it is important that the resulting RNA transcript be cleaved into the individual mature RNA molecules of the present invention. To this end, it is particularly desirable for each of the plurality of monomeric DNA sequences to also encode a cis-acting ribozyme that can cleave the immature RNA transcript of the DNA molecule to yield multiple copies of the RNA molecule. Although any ribozyme sequence can be utilized, a hammerhead ribozyme sequence (Haseloff and Gerlach, "Simple RNA Enzymes with New and High Specific Endoribonucleases Activities," *Nature* 334:585-591 (1988), which is hereby incorporated by reference in its entirety) is preferred because of its simplified and efficient structure. The sequence encoding the hammerhead ribozyme is incorporated into each of the plurality of monomeric DNA sequences, resulting in the hammerhead ribozyme being located at one end of each monomeric unit of the immature RNA transcript. The immature RNA transcript is self-cleaved by the cis-acting ribozyme to yield the mature RNA molecule. See U.S. Pat. No. 6,458,559 to Shi et al., which is hereby incorporated by reference in its entirety.

Once the DNA molecule or engineered gene of the present invention has been constructed, it can be incorporated into cells using conventional recombinant DNA technology. Generally, this involves inserting the DNA molecule or engineered gene into an expression system to which the DNA molecule or engineered gene is heterologous (i.e., not normally present). The heterologous DNA molecule or engineered gene is inserted into the expression system or vector in proper sense orientation. The vector contains the necessary elements for their persistent existence inside cells and for the transcription of the RNA molecule of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant or engineered genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology, vol.* 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156:119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucleic Acids Research* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118: 401-415 (1993), which is hereby incorporated by reference in its entirety), and any derivatives thereof. Suitable vectors are continually being developed and identified.

A variety of host-vector systems may be utilized to express the RNA molecule-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retroviral vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecules or engineered genes encoding the RNA molecules, as described above, have been cloned into an expression system, they are ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety. Suitable host cells include, but are not limited to, bacteria, yeast, mammalian cells, insect cells, plant cells, and the like. The host cell is preferably present either in a cell culture or in a whole living organism.

Plant tissues suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to control expression of a target molecule (e.g., a protein or nucleic acid) using an RNA molecule of the present invention. Transformed cells can be regenerated into whole plants such that the expressed RNA molecule regulates the function or activity of the target protein in the intact transgenic plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100, 792, all to Sanford, et al., which are hereby incorporated by reference in its entirety.

Another method of introducing the engineered gene of the present invention into a host cell is fusion of protoplasts with other entities, either minicells, cells, lysosomes, or other fusible lipid-surfaced bodies that contain the DNA molecule (Fraley et al., "Expression of Bacterial Genes in Plant Cells," *Proc. Natl. Acad. Sci. USA,* 80:4803-4807 (1983), which is hereby incorporated by reference in its entirety).

The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," *Proc. Natl. Acad. Sci. USA,* 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," *Mol. Gen. Genetics,* 202:179-85 (1985), which is hereby incorporated by reference in its entirety). The genetic material may also be transferred into the plant cell using polyethylene glycol (Krens et al., "In Vitro Transformation of Plant Protoplasts with TI-Plasmid DNA," *Nature,* 296:72-74 (1982), which is hereby incorporated by reference in its entirety).

One technique of transforming plants with the DNA molecules in accordance with the present invention is by contacting the tissue of such plants with an inoculum of a bacteria transformed with a vector comprising a DNA molecule or an engineered gene in accordance with the present invention. Generally, this procedure involves inoculating the plant tissue with a suspension of bacteria and incubating the tissue for 48 to 72 hours on regeneration medium without antibiotics at 25-28° C.

Bacteria from the genus *Agrobacterium* can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHAl 05) is particularly useful due to its well-known ability to transform plants.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, "Transgenic Plants as Tools to Study the Molecular Organization of Plant Genes," *Science* 237:1176-83 (1987), which is hereby incorporated by reference in its entirety).

After transformation, the transformed plant cells must be regenerated.

Plant regeneration from cultured protoplasts is described in Evans et al., *Handbook of Plant Cell Cultures, Vol.* 1, Mac-Millan Publishing Co., New York (1983) and Vasil (ed.), *Cell Culture and Somatic Cell Genetics of Plants*, Acad. Press, Orlando, Vol. I (1984) and Vol. III (1986), which are hereby incorporated by reference in their entirety.

It is known that practically all plants can be regenerated from cultured cells or tissues.

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, and cells recovered directly from a mammalian organism.

In addition to in vitro transformation of mammalian cells, in vivo transformation can also be achieved. Thus, another aspect of the present invention relates to a transgenic non-human organism whose somatic and/or germ cell lines contain an engineered gene of the present invention (e.g., encoding an RNA molecule) which, upon expression thereof in the presence of a target molecule, modifies (e.g., inhibits) activity of the target molecule, wherein said modification (e.g., inhibition) is carried out in somatic and/or germ cells of the organism to rectify a condition associated with, e.g., overexpression of the target molecule in somatic and/or germ cells of the organism. The target molecule can be any target used in the selection process, preferably a protein or nucleic acid. As described in U.S. Pat. No. 6,458,559 to Shi et al., which is hereby incorporated by reference in its entirety, RNA aptamer expression in a transgenic eukaryote can overcome a nonlethal phenotype associated with overexpression of a protein product.

The transgenic non-human organism is preferably a multicellular organism, such as a plant (as described supra), an animal, or an insect. The plant can be a monocot or a dicot. The animal can be a mammal, an amphibian, a fish, a reptile, or a bird. Preferred transgenic mammals of the present invention include sheep, goats, cows, dogs, cats, all non-human primates, such as monkeys and chimpanzees, and all rodents, such as rats and mice. Preferred insects include all species of *Drosophila*, particularly *Drosophila melanogaster*. It should be appreciated that the above-listed species or classes are only intended to be exemplary and, as such, are non-limiting.

Procedures for making transgenic animals are well known. One means available for producing a transgenic animal (e.g., a mouse) is as follows: female mice are mated, and the resulting fertilized eggs are dissected out of their oviducts. The eggs are stored in an appropriate medium such as M2 medium (Hogan B. et al. *Manipulating the Mouse Embryo, A Laboratory Manual*, Cold Spring Harbor Laboratory (1986), which is hereby incorporated by reference in its entirety). A DNA or cDNA molecule is purified from a vector by methods well known in the art. As described above, inducible promoters may be fused with the coding region of the DNA to provide an experimental means to regulate expression of the transgene. Alternatively, or in addition, tissue specific regulatory elements may be fused with the coding region to permit tissue-specific expression of the transgene. The DNA, in an appropriately buffered solution, is put into a microinjection needle (which may be made from capillary tubing using a pipet puller), and the egg to be injected is put in a depression slide. The needle is inserted into the pronucleus of the egg, and the DNA solution is injected. The injected egg is then transferred into the oviduct of a pseudopregnant mouse (i.e., a mouse stimulated by the appropriate hormones to maintain pregnancy, but which is not actually pregnant), where it proceeds to the uterus, implants, and develops to term.

Alternatively, transgenic animals can be prepared by inserting a DNA molecule into a blastocyst of an embryo or into embryonic stem cells.

Transgenic organisms of the present invention are useful for modulating gene expression and protein activity in processes including, but not limited to, drug target validation, crop yield enhancement, fermentation, bioremediation, biodeterioration, and biotransformation.

Related aspects of the present invention involve methods of expressing an RNA molecule in a cell which include introducing either a DNA molecule of the present invention or an engineered gene of the present invention into a cell under conditions effective to express the RNA molecule. As described above, the conditions under which expression will occur are dependent upon the particular promoter or other regulatory sequences employed.

Another aspect of the present invention relates to a method of modifying the activity of a target molecule (e.g., a beta-amyloid peptide), either in vitro or in vivo (i.e., in a cell), which includes providing a nucleic acid molecule of the present invention in a cell, wherein the RNA aptamer has affinity for one or more target molecules sufficient to modify activity of the one or more target molecule(s). This method can be carried out in vivo by directly introducing an RNA molecule or a DNA molecule into the cell, or by introducing into the cell (prior to the step of expressing) a DNA molecule (such as a DNA construct, engineered gene, or expression vector containing the same) encoding the RNA molecule. As described above, expression of the DNA molecule can be under the control of any one of a variety of regulatory sequences such as promoters, preferably inducible promoters. The cell can be in an in vitro environment, in an in vivo cell culture, or in vivo within an organism.

Modification of the activity of the target molecule(s) may include, without limitation, inhibiting the activity of the target molecule(s), promoting the activity of the target molecule(s), increasing the stability of the target molecule(s), and/or decreasing the stability of the target molecule(s).

To the extent that the activity of the target molecule (e.g., a protein) can be modified to achieve a therapeutic change in phenotype, the nucleic acid molecules can be used as therapeutic agents, alone or in combination with other therapeutic agents. For treatment of a patient, the nucleic acid molecules can be delivered directly as a part of a therapeutic composition. Alternatively, treatment of a patient may be carried out by delivering the nucleic acid molecules through methods of gene therapy. Nucleic acid molecules may be directly introduced into cells of tissues in vivo using delivery vehicles such as adenoviral vectors, retroviral vectors, DNA virus vectors, and colloidal dispersion systems. They may also be introduced into cells in vivo using physical techniques such as microinjection and electroporation or chemical methods such as coprecipitation and incorporation of nucleic acid into liposomes.

Adenovirus gene delivery vehicles can be readily prepared and utilized given the disclosure provided in Berkner, "Development of Adenovirus Vectors for the Expression of Heterologous Genes," *Biotechniques* 6:616-627 (1988) and Rosenfeld et al., "Adenovirus-Epithelium *In Vivo*," *Science* 252: 431-434 (1991), WO 93/07283, WO 93/06223, and WO 93/07282, which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Adeno-associated viral gene delivery vehicles can be constructed and used to deliver into cells a nucleic acid molecule of the present invention. The use of adeno-associated viral gene delivery vehicles in vitro is described in Chatterjee et al., "Dual Target Inhibition of HIV-1 In Vitro by Means of an Adeno-Associated Virus Antisense Vector," *Science* 258: 1485-1488 (1992); Walsh et al., "Regulated High Level Expression of a Human Gamma-Globin Gene Introduced into Erythroid Cells by an Adeno-Associated Virus Vector," *Proc. Nat'l. Acad. Sci. USA* 89:7257-7261 (1992); Walsh et al., "Phenotypic Correction of Fanconi Anemia in Human Hematopoietic Cells with a Recombinant Adeno-Associated Virus Vector," *J. Clin. Invest.* 94:1440-1448 (1994); Flotte et al., "Expression of the Cystic Fibrosis Transmembrane Conductance Regulator from a Novel Adeno-Associated Virus Promoter," *J. Biol. Chem.* 268:3781-3790 (1993); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); Miller et al., "Recombinant Adeno-associated Virus (rAAV)-Mediated Expression of a Human Gamma-Globin Gene in Human Progenitor-Derived Erythroid Cells," *Proc. Nat'l Acad. Sci. USA* 91:10183-10187 (1994); Einerhand et al., "Regulated High-level Human Beta-Globin Gene Expression in Erythroid Cells Following Recombinant Adeno-Associated Virus-Mediated Gene Transfer," *Gene Ther.* 2:336-343 (1995); Luo et al., "Adeno-Associated Virus 2-Mediated Gene Transfer and Functional Expression of the Human Granulocyte-Macrophage Colony-Stimulating Factor," *Exp. Hematol.* 23:1261-1267 (1995); and Zhou et al., "Adeno-Associated Virus 2-Mediated Transduction and Erythroid Cell-Specific Expression of a Human β-Globin Gene," *Gene Ther.* 3:223-229 (1996), which are hereby incorporated by reference in their entirety. In vivo use of these vehicles is described in Flotte et al., "Stable In Vivo Expression of the Cystic Fibrosis Transmembrane Conductance Regulator with an Adeno-Associated Virus Vector," *Proc. Nat'l Acad. Sci. USA* 90:10613-10617 (1993); and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety.

Retroviral vectors which have been modified to form infective transformation systems can also be used to deliver into cells a nucleic acid molecule of the present invention. One such type of retroviral vector is disclosed in U.S. Pat. No. 5,849,586 to Kriegler et al., which is hereby incorporated by reference in its entirety.

Alternatively, a colloidal dispersion system can be used to deliver the nucleic acid molecule. Colloidal dispersion systems include macromolecule complexes, nanocapsules, microspheres, beads, and lipid-based systems including oil-in-water emulsions, micelles, mixed micelles, and liposomes. The preferred colloidal system of this invention is a lipid preparation including unilamellar and multilamellar liposomes.

Liposomes are artificial membrane vesicles that are useful as delivery vehicles in vitro and in vivo. It has been shown that large unilamellar vesicles (LUV), which range in size from about 0.2 to about 4.0 μM, can encapsulate a substantial percentage of an aqueous buffer containing nucleic acid molecules (Fraley et al., *Trends Biochem. Sci.* 6:77 (1981), which is hereby incorporated by reference in its entirety). In addition to mammalian cells, liposomes have been used for delivery of polynucleotides in yeast and bacterial cells. For a liposome to be an efficient transfer vehicle, the following characteristics should be present: (1) encapsulation of the nucleic acid molecules at high efficiency while not compromising their biological activity; (2) substantial binding to host organism cells; (3) delivery of the aqueous contents of the vesicle to the cell cytoplasm at high efficiency; and (4) accurate and effective expression of genetic information (Mannino et al., "Liposome Mediated Gene Transfer," *Biotechniques* 6:682 (1988), which is hereby incorporated by reference in its entirety). In addition to such LUV structures, multilamellar and small unilamellar lipid preparations which incorporate various cationic lipid amphiphiles can also be mixed with anionic DNA molecules to form liposomes (Feigner et al., "Lipofection: A Highly Efficient, Lipid-Mediated DNA-Transfection Procedure," *Proc. Natl. Acad. Sci. USA* 84(21):7413 (1987), which is hereby incorporated by reference in its entirety).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and typically the presence of divalent cations. The appropriate composition and preparation of cationic lipid amphiphile/DNA formulations are known to those skilled in the art, and a number of references which provide this information are available (e.g., Bennett et al., "Considerations for the Design of Improved Cationic Amphiphile-based Transfection Reagents," *J. Liposome Research* 6(3):545 (1996), which is hereby incorporated by reference in its entirety).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids N-[1-(2,3-dioleoyloxy)propyl]-N,N,N,-trimethyl ammonium methyl-sulfate, N-[2,3-dioleoyloxy)propyl]-N,N,N-trimethyl ammonium chloride, and DCcholesterol, the polyvalent lipids LipofectAMINE™, dioctadecylamidoglycyl spermine, Transfectam®, and other amphiphilic polyamines. These agents may be prepared with helper lipids such as dioleoyl phosphatidyl ethanolamine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

The cocaine-binding-site ligands and/or cocaine-binding-site RNA aptamers of the present invention can be administered orally, parenterally, for example, subcutaneously, intravenously, intramuscularly, intraperitoneally, by intranasal inhalation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The cocaine-binding-site ligands and/or cocaine-binding-site RNA aptamers of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the cocaine-binding-site ligands and/or cocaine-binding-site RNA aptamers of the present invention may be incorporated with excipients and used in the form of tablets, capsules, elixirs, suspensions, syrups, and the like. Such compositions and preparations should contain at least 0.1% of active compound. The percentage of the cocaine-binding-site ligands and/or cocaine-binding-site RNA aptamers of the present invention in these compositions may, of course, be varied and may conveniently be between about 2% to about 60% of the weight of the unit. The amount of the cocaine-binding-site ligands and/or cocaine-binding-site RNA aptamers of the present invention in such therapeutically useful compositions is such that a suitable dosage will be obtained. Preferred compositions according to the present invention are prepared so that an oral dosage unit contains between about 1 and 250 mg of the cocaine-binding-site ligands and/or cocaine-binding-site RNA aptamers of the present invention.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The cocaine-binding-site ligands and/or cocaine-binding-site RNA aptamers of the present invention may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The cocaine-binding-site ligands and/or cocaine-binding-site RNA aptamers of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

These aspects of the present invention are further illustrated by the examples below.

EXAMPLES

The following examples are provided to illustrate embodiments of the present invention, but they are by no means intended to limit its scope. All of the references cited in the below Examples are hereby incorporated by reference in their entirety.

Example 1

Aptamer Sequence Analysis

The RNA aptamer sequences reported to bind with high affinity to the Aβ(1-40) peptide were analyzed by applicants using the online software TEIRESIAS. This sequence analysis led to the identification of motif similarity between the cocaine-binding site of the nicotinic acetylcholine receptor and the beta-amyloid peptide, allowing for the identification of a cocaine-binding site on the beta-amyloid peptide to which ligands of the cocaine-binding site on the receptor could bind, interact with, and affect peptide aggregation.

Example 2

Whole-Cell Current Recordings

Carbamoylcholine-induced currents were recorded using the whole-cell configuration at room temperature (22-23° C.), pH 7.4, and a transmembrane voltage of −60 mV. The currents were amplified using an Axopatch 200B amplifier (Axon Instruments, Union City, Calif.) and filtered at 1 kHz (using a four-pole low-pass Bessel filter incorporated in the Axopatch 200B amplifier). The filtered signal was digitized using a Labmaster DMA 100 kHz digitizing board (Scientific Solutions, Chelmsford, Mass.) controlled by Clampex 8.1 data acquisition software (Axon Instruments, Union City, Calif.). Typical digitizing frequencies were 2-5 kHz. The recording glass pipets were pulled from borosilicate glass (World Precision Instruments Inc., Sarasota, Fla.), using a two-stage puller (L/M 3 P-A, Adams & List, NY) and a flame polisher (MF-83, Narishige, Tokyo, Japan). The recording pipet contained $BC_3H1$ intracellular buffer, 140-mM KCl, 10-mM NaCl, 2-mM $MgCl_2.6H_2O$, 1-mM EGTA, and 25-mM HEPES, adjusted to pH 7.4 using 1N KOH. The bath solution contained 145-mM NaCl, 5.3-mM KCl, 1.8-mM $CaCl_2.2H_2O$, 1.7-mM $MgCl_2.6H_2O$, and 25-mM HEPES, adjusted to pH 7.4 using 5 N NaOH. The resistance of the recording electrode filled with the buffer solution was typically 3-5MΩ, and the series resistance was 5-6 MΩ. A series resistance compensation of 60-80% was used, via an Axopatch 200B amplifier (Axon Instruments). Typical maximum currents at 100-μM carbamoylcholine (control concentration) were 2-13 nA.

Example 3

Transient Kinetic Techniques

To investigate the mechanism of inhibition of the nicotinic acetylcholine receptor by amyloid peptides and alleviation of the inhibition, two rapid kinetic techniques (reviewed Breitinger et al., "Fast Kinetic Analysis of Ligand-Gated Ion Channels," *Neuroscientist* 7:95-103 (2001); Hess et al., "Development and Application of Caged Ligands for Neurotransmitter Receptors in Transient Kinetic and Neuronal Circuit Mapping Studies," *Methods in Enzymology* 291:443-473 (1998), which are hereby incorporated by reference in their entirety) were used. The approach used in these mechanistic investigations has been described in detail (Hess et al., "Mechanism-Based Discovery of Ligands that Prevent Inhibition of the Nicotinic Acetylcholine Receptor by Cocaine and MK-801," *Proc. Natl. Acad. Sci. USA* 97:13895-13900 (2000); Hess et al., "Reversing the Action of Noncompetitive Inhibitors (MK-801 and Cocaine) on a Protein (Nicotinic Acetylcholine Receptor)-Mediated Reaction," *Biochemistry* 42:6106-6114 (2003); Chen et al., "Mechanism-Based Discovery of Small Molecules that Prevent Non-Competitive Inhibition by Cocaine and MK-801 Mediated by Two Different Sites on the Nicotinic Acetylcholine Receptor," *Biochemistry* 43:10149-10156 (2004), which are hereby incorporated by reference in their entirety). Both techniques were used to study receptor inactivation and to measure the rate of receptor desensitization.

Example 4

Cell-Flow Method

This transient kinetic technique is utilized for three purposes: to measure current amplitudes corrected for the receptor desensitization that occurs during the rising phase of the current, to calibrate the concentration of neurotransmitter released from caged neurotransmitter in the laser-pulse photolysis technique, and to measure the rate of receptor desensitization. From the corrected current amplitude information about the dissociation constant of the receptor-activating ligand is obtained (Hess et al., "Development and Application of Caged Ligands for Neurotransmitter Receptors in Transient Kinetic and Neuronal Circuit Mapping Studies," *Methods in Enzymology* 291:443-473 (1998), which is hereby incorporated by reference in its entirety). If the experiments are carried out in presence of a constant concentration of activating ligand and various concentrations of an inhibitor, information about the dissociation constant of the inhibitor is obtained. The technique has a 10-millisecond time resolution. After a gigaseal is achieved by suction on the cell via the current-recording electrode to which it is attached, the cell is lifted from the substratum and suspended from the electrode that is placed about 50 μm away from a 150-nm diameter porthole in a U-tube that delivers solution to the cell surface. Solutions flow at rates of 2.5 cm $s^{-1}$ over the single, suspended cell (Hess et al., "Chemical Kinetic Measurements of Transmembrane Processes Using Rapid Reaction Techniques: Acetylcholine Receptor," *Ann. Rev. Biophys. Biophys. Chem.* 16:507-534 (1987), which is hereby incorporated by reference in its entirety). Because the orientation of the porthole with respect to the cell is critical, a U-tube device designed by Krishtal et al., "A Receptor for Protons in the Nerve Cell Membrane," *Neuroscience* 5:2325-2327 (1980), which is hereby incorporated by reference in its entirety, was modified so that the porthole is stationary and mixing of solutions occurs before they leave the porthole. Stainless steel for the U-tube was used because the internal diameter is more consistent than other materials sometimes used. A modified U-tube that enables one to flow solutions of different composition over the cell, and to pre-incubate ligands with the cell, is described in detail by Niu et al., "Chemical Kinetic Investigations of Neurotransmitter Receptors on a Cell Surface in the ns Time Region," *Techniques in Protein Chem.* VII:139-149 (1996), which is hereby incorporated by reference in its entirety. As many as 20 measurements have been made with the same cell. At the flow rates used, the current must be corrected for desensitization (Udgaonkar et al., "Chemical Kinetic Measurements of a Mammalian Acetylcholine Receptor by a Fast-Reaction Technique," *Proc. Nat. Acad. Sci. USA* 84:8758-8762 (1987), which is hereby incorporated by reference in its entirety). In this regard, the reported measurements differ from others. If higher flow rates are used, the seal between the cell membrane and the recording electrode becomes unstable, requiring measurements to be made with more cells. The ability to make many measurements with each cell decreases the experimental error. Such problems are treated in several textbooks (e.g., Bevington, P. R., *Data Reduction and Error Analysis for the Physical Sciences* (McGraw Hill, New York) (1969), which is hereby incorporated by reference in its entirety). An additional problem with high flow rates is that the flow of solution, containing a known ligand concentration, can become turbulent rather than laminar, leading to changes in ligand concentration in an unknown way. Since receptor density varies from cell to cell, the data must be normalized. Thus, at least one measurement is made with each cell at a specific concentration of neurotransmitter, in addition to the measurements at different concentrations.

Example 5

Data Analysis of Whole Cell Current Recordings

The maximum amplitude of the current is a measure of the concentration of open-receptor channels. In cell-flow experiments with 100-μM carbamoylcholine, the observed rise time of the whole-cell current to its maximum value, characteristic of the time for carbamoylcholine to equilibrate with the cell surface receptors, was 60-200 ms. Receptor desensitization during this time can be significant. Therefore, the current was corrected, as described previously (Udgaonkar et al., "Chemical Kinetic Measurements of a Mammalian Acetylcholine Receptor by a Fast-Reaction Technique," *Proc. Natl. Acad. Sci. U.S.A.* 84:8758 (1987); Hess et al., "Chemical Kinetic Measurements of Transmembrane Processes using Rapid Reaction Techniques Acetylcholine Receptor," *Annu. Rev. Biophys. Biophys. Chem.* 16:506 (1987), which is hereby incorporated by reference in its entirety), for desensitization that occurs during the time it takes carbamoylcholine to equilibrate with the receptors on the cell surface. This provides the maximum current amplitude corrected for the desensitization. The cells tested showed a double-exponential current decay. Data were analyzed offline on a PC, and the time constants for the rising and decaying phases of the whole-cell current were obtained by using a nonlinear least-squares fitting program with Microcal Origin 3.5 software (Origin Lab Corp., Northampton, Mass.). The apparent dissociation constant $K_I$ of the β-amyloid-specific aptamer B55 from the nicotinic acetylcholine receptor is obtained according to the equation $$\frac{A_O}{A_I} = 1 + \frac{[I]}{K_I}.$$

$A_O$ and $A_I$ represent the amplitudes of the current maxima obtained at a given concentration of activating ligand in absence and presence of a noncompetitive inhibitor, respectively. [I] represents the inhibitor concentration and $K_I$ the observed dissociation constant of the inhibitor.

Example 6

Preparation of Aβ(1-40) Peptide for Aggregation Studies

Aβ(1-40) stock solutions were prepared by dissolving the peptide in 1,1,1,3,3,3-hexafluoro-2-propanol (HFIP) to yield a 5 mg/ml solution, i.e. 1 mg of peptide is dissolved in 200 μL HFIP. The 5 mg/mL solution of peptide in HFIP is then sonicated for 30-60 minutes. The sonicated 5 mg/mL solution of peptide in HFIP is then diluted to 250 μM (~1 mg/mL) in autoclaved double-distilled water to form the Aβ(1-40) stock solution, which after vortexing is sonicated for an additional 30-60 minutes. The stock solution was dispensed into 100 μL aliquots that were stored at −20° C. for Thioflavin T fluorescence assay aggregation experiments and thawed immediately before the experiments.

Example 7

Thioflavin T Fluorescence Assay

Thioflavin T associates rapidly with aggregated fibrils of Aβ(1-40), giving rise to a new excitation (ex) (absorption) maximum at 450 nm and enhanced emission (em) at 482 nm, as opposed to 350 nm (ex) and 438 nm (em) for the free dye (LeVine, "Thioflavine T Interaction with Synthetic Alzheimer's Disease β-Amyloid Peptides: Detection of Amyloid Aggregation in Solution," *Protein Sci.* 2:404 (1993); LeVine, "Quantification of β-sheet Amyloid Fibril Structures with Thioflavin T," *Methods Enzymol.* 309:274 (1999), which are hereby incorporated by reference in their entirety). The fluorescence of Thioflavin T in the presence of β-amyloid fibrils is pH-dependent, reaching a maximum at approximately pH 8.5 (LeVine, "Thioflavine T Interaction with Synthetic Alzheimer's Disease β-Amyloid Peptides: Detection of Amyloid Aggregation in Solution," *Protein Sci.* 2:404 (1993); LeVine, "Quantification of β-sheet Amyloid Fibril Structures with Thioflavin T," *Methods Enzymol.* 309:274 (1999), which are hereby incorporated by reference in their entirety). 50-μM Aβ(1-40) solutions were made in 50-mM sodium phosphate, 100-mM sodium chloride, and 0.02% sodium azide buffer, adjusted to pH 7.4. These solutions were incubated, in the absence and presence of different concentrations of cocaine and ecgonine methyl ester at 37° C. and gently shaken at 100 rpm for 2 days. 40 μL of the reaction solutions were then added to 500 fit of 5-μM Thioflavin T in 50-mM glycine/sodium hydroxide, pH 8.5. The fluorescence was determined at an excitation wavelength of 429 nm (2.5-nm slit) and an emission wavelength of 489 nm (10-nm slit). Readings for each sample were done in triplicate and the average was taken as the final reading. The fluorescence of a solution containing the same concentration of Thioflavin T alone was subtracted from the sample's averaged reading. It was verified that neither cocaine nor ecgonine methyl ester quenched the fluorescence of Thioflavin T at the concentrations tested. The results were then normalized against a solution containing 50-μM Aβ(1-40) peptide alone. The data from three identical samples from separate experiments were then used to compute the mean and standard deviation (error bars) reported in FIG. 4A.

Example 8

Electrophoretic Mobility Shift Assay

The $pK_a$ of cocaine is 8.6; therefore, at pH 7.4 the compound is predominantly neutral and has no electrophoretic mobility. On the other hand, the theoretical isoelectric point of the Aβ(1-40) peptide is 5.37 (Wiltfang et al., "Highly Conserved and Disease-Specific Patterns of Carboxyterminally Truncated Aβ Peptides 1-37/38/39 in Addition to 1-40/42 in Alzheimer's Disease and in Patients with Chronic Neuroinflammation," *J. Neurochem.* 81:481-496 (2002), which is hereby incorporated by reference in its entirety). At pH 7.4 the Aβ(1-40) peptide has a net negative charge of ~−3 (Ege et al., "Insertion of Alzheimer's Aβ340 Peptide into Lipid Monolayers," *Biophys. J.* 87:1732-1740 (2004), which is hereby incorporated by reference in its entirety). Therefore, if cocaine binds to the Aβ(1-40) peptide, the complex will travel into the gel; free cocaine does not travel into the gel, since it is neutral at pH 7.4 (FIG. 3). A 20% native acrylamide gel in TBE (89-mM Tris/89-mM boric acid/2 mM-EDTA) adjusted to pH 7.4 is prepared (Sambrook, *Molecular Cloning: A Laboratory Manual*, Cold Spring Harbor Lab. Press, Cold Spring Harbor, N.Y. (1989), which is hereby incorporated by reference in its entirety). Samples of [$^3$H]-cocaine and Aβ(1-40) peptide mixed in TBE buffer are incubated for 1 hr at room temperature. After incubation, 5% glycerol and 0.04% bromophenol blue are added and the mixture is then loaded on to the gel, which is run at room temperature. The gel is removed after 2 hr and imaged by using a tritium-sensitive phosphorimaging plate (BAS-TR2040, Fuji). The imaging plate is then scanned by using a Molecular Dynamics Storm 860 PhosphorImager, and band intensities are quantified by using the IMAGEQUANT software from Molecular Dynamics. The same gel is later stained with Coomassie® Blue (Bio-Rad Laboratories) to determine the position of the Aβ(1-40) band and to compare its position to the cocaine band that shifts in the presence of the peptide (FIG. 3). The dissociation constant of cocaine from the Aβ(1-40) peptide can then be calculated (Fried et al., "Measurement of Protein-DNA Interaction Parameters by Electrophoresis Mobility Shift Assay", *Electrophoresis* 10:366-376 (1989), which is hereby incorporated by reference in its entirety). Since the Aβ(1-40) and Aβ(1-42) peptides differ only by two non-charged (hydrophobic) amino acids in their carboxy terminals, their isoelectric points are identical (Wiltfang et al., "Highly Conserved and Disease-Specific Patterns of Carboxyterminally Truncated Aβ Peptides 1-37/38/39 in Addition to 1-40/42 in Alzheimer's Disease and in Patients with Chronic Neuroinflammation," *J. Neurochem.* 81:481-496 (2002), which is hereby incorporated by reference in its entirety) and, therefore, the Aβ(1-42) peptide would also carry a net negative charge close to −3 at pH 7.4. Thus, the same experiment can be done with the Aβ(1-42) peptide.

Example 9

Discovery of a Regulatory Site on Beta-Amyloid Peptides

A beta-amyloid peptide with 40 residues [Aβ(1-40)] is associated with Alzheimer's Disease. Recently, RNA polymers (aptamers) were isolated that bind to the peptide (Ylera et al., "Selection of RNA Aptamers to the Alzheimer's Disease Amyloid Peptide," *Biochem. Biophys. Res. Commun.* 290:1583-1588 (2002), which is hereby incorporated by reference in its entirety). Applicants analyzed the published sequences and found a 7-nucleotide consensus sequence (UUCACCG) present in all 18 aptamers (Table 1). This same consensus sequence was also found in 14 inhibitory RNA Class I aptamers previously isolated. The RNA Class I aptamers bind to an inhibitory cocaine-binding site of the nicotinic acetylcholine receptor (Ulrich et al., "In Vitro Selection of RNA Molecules that Displace Cocaine from the Membrane-Bound Nicotinic Receptor," *Proc. Natl. Acad. Sci. USA* 95:14051-14056 (1998), which is hereby incorporated by reference in its entirety). Table 2 shows the consensus sequence present in both aptamers. The number below each nucleotide of the sequence indicates the number of times the nucleotide appears in the 18 different aptamers specific for the Aβ(1-40) peptide (Table 2A) or in the 14 different Class I aptamers that are specific for the inhibitory cocaine-binding site of the muscle-type nicotinic acetylcholine receptor (Table 2B). This analysis indicates that the fidelities of the different nucleotides in each consensus sequence share a similar pattern; the high fidelity portion of the sequence, namely ACCG, is strongly conserved in both consensus sequences (Table 2).

TABLE 1

| Aptamer | Structure |
|---|---|
| B5 | 5'-CUCGAUCACCGUAAGGACAUCUACGUAAGUGUAAUGCGGCUUGUUUUCCCCAUGCGUCUGCAUAUCUGUU-3' (SEQ ID NO: 24) |
| B15 | 5'-UUUACCGUAAGGCCUGUCAUCGUUUGACAGCGGCUUGUUGACCCUUCCACUAUGUGUGCCUGUAAUG-3' (SEQ ID NO: 25) |
| B19 | 5'-ACUUCGUCUUGCAGCGCGGCUUGUCUCUUCCCACAUCCGUUCUAUCGGUAUGACUCUUUUCCGUAAGGUCA-3' (SEQ ID NO: 26) |
| B27 | 5'-UUUACCGUAAGGCCUGUCUUCGUUUGACAGCGGCUUGUUGACCCUCACACUUUGUACCUCUGCCUG-3' (SEQ ID NO: 27) |
| B28 | 5'-CUCGAUCACCGUAAGGACAUCUACAUAAGUGUAAUGCGGCUUGUUUUCCCCAUGCAUCUGCAUAUCUGU-3' (SEQ ID NO: 28) |
| B36 | 5'-UGUCCACCGUAGAUUGUAAACUAUCGCGUAAAGCGAAGUUUAUGUGGCUUGUUUUCCCACGCCUUG-3' (SEQ ID NO: 29) |
| B44 | 5'-CUCGAUCACCGUAAGGACAUUUACGUAAGUGUAAUGCGGCUUGUUUUCCCCAUGCGUCUGCAUAUCUGU-3' (SEQ ID NO: 30) |
| B55 | 5'-UUUACCGUAAGGCCUGUCUUCGUUUGACAGCGGCUUGUUGACCCUCACACUUUGUACCUGCUGCCAA-3' (SEQ ID NO: 31) |
| B59 | 5'-UCCACCGUAAGAUUGUAAACUAUCGGGUAAAGACGAAGUUUAUGUGGCUUGUUUCCCACCGCCUUGCC-3' (SEQ ID NO: 32) |
| B61 | 5'-UGUCCACCGUAAGAUUGUAAACUAUCGUAAAGACGAAGUUUAUGUGGCUUGUUUUCCCACCGCCUUGCC-3' (SEQ ID NO: 33) |
| B64 | 5'-UUUACCGUAAGGCCUGUCAUCGUUUGACAGCGGCUUGUUGACCCUUCCACUAUGUGUGCCUGUAAUG-3' (SEQ ID NO: 34) |
| B65 | 5'-UUUACCGUAAGGCCUGUCUUCGUUUGACAGCGGCUUGUUGACCCACACACUUUGUCCCGGCUGCAG-3' (SEQ ID NO: 35) |
| B69 | 5'-UUUACCGUAAGGCCUGUCUUCUUUUGACAGCGGCUUGUUGACCCUCACGCUUUGUCCCUGCUGUACCUG-3' (SEQ ID NO: 36) |
| B76 | 5'-UCCACCGUAAGAUUGUAAACUAUCGCGUAAAAGACGAAGUUUAUGUGGCUUGUUUUCCCACCGCCUUG-3' (SEQ ID NO: 37) |
| B78 | 5'-ACUUCGUCUUGCAGCGCGGCUUGUCUCUUCCCACAUCCGUUCUAUCGGUAUGACUUUUUCCGUAAGGUCA-3' (SEQ ID NO: 38) |

TABLE 1-continued

| Aptamer | Structure |
|---|---|
| B108 | 5'-UCCACCGUAAGAUUGUAAACUAUCGCGUAAAGACGAAGUUUAUGUGGCUUGUUUCCCACCACCUUGCG-3' (SEQ ID NO: 39) |
| B111 | 5'-UUUACCGUAAGGCCUGUCUUCGUUUGACAGCGGCUUGUUGACCCUCACGCUUUGUCCCAUGCCCGUC-3' (SEQ ID NO: 40) |
| B124 | 5'-CUCG<u>AUCACCGUAAGG</u>ACAUUUACGUAAGUGUAAUGCGGCUUGUUUUCCCCAUGCGUUUGCAUAUCUGUG-3' (SEQ ID NO: 41) |
| Consensus | UUCACCGUAAGG (SEQ ID NO: 5) |
| Position | 1 2 3 4 5 6 7 8 9 10 11 12 |
| Consensus | U U C A C C G U A A G G |
| Frequency | 14 12 10 16 18 18 18 18 18 18 17 12 |

18 RNA aptamer sequences reported to bind the Aβ(1-40) peptide were analyzed to determine if they contained a consensus sequence similar to that found in aptamers binding to molecules other than the β-amyloid peptides. The consensus region of the aptamers is typed in bold. Underlined is the portion of the consensus sequence that overlaps the consensus sequence of RNA aptamers that bind to the inhibitory cocaine-binding site of the nicotinic acetylcholine receptor and noncompetitively inhibit the receptor. The section at the end gives the nucleotides and their pertinent positions and frequencies in the consensus region.

TABLE 2

| A. | | | | | | | B. | | | | | |
|---|---|---|---|---|---|---|---|---|---|---|---|---|
| U | U | C | A | C | C | G | <u>U</u> | <u>U</u> | <u>C</u> | <u>A</u> | <u>C</u> | <u>C</u> | <u>G</u> |
| 9 | 9 | 9 | 10 | 14 | 13 | 14 | <u>14</u> | <u>12</u> | <u>10</u> | <u>16</u> | <u>18</u> | <u>18</u> | <u>18</u> |

Table 2A shows the consensus sequence of the 14 RNA aptamers with a 40-nucleotide variable region that bind to the inhibitory cocaine-binding site of the nicotinic acetylcholine receptor and noncompetitively inhibit the receptor. Table 2B shows the consensus sequence of the 18 Aβ(1-40)-binding RNA aptamers with a 70-nucleotide variable region. The number below each nucleotide indicates the number of times the nucleotide occurs in the sequence in the aptamers examined.

Figure 1A:
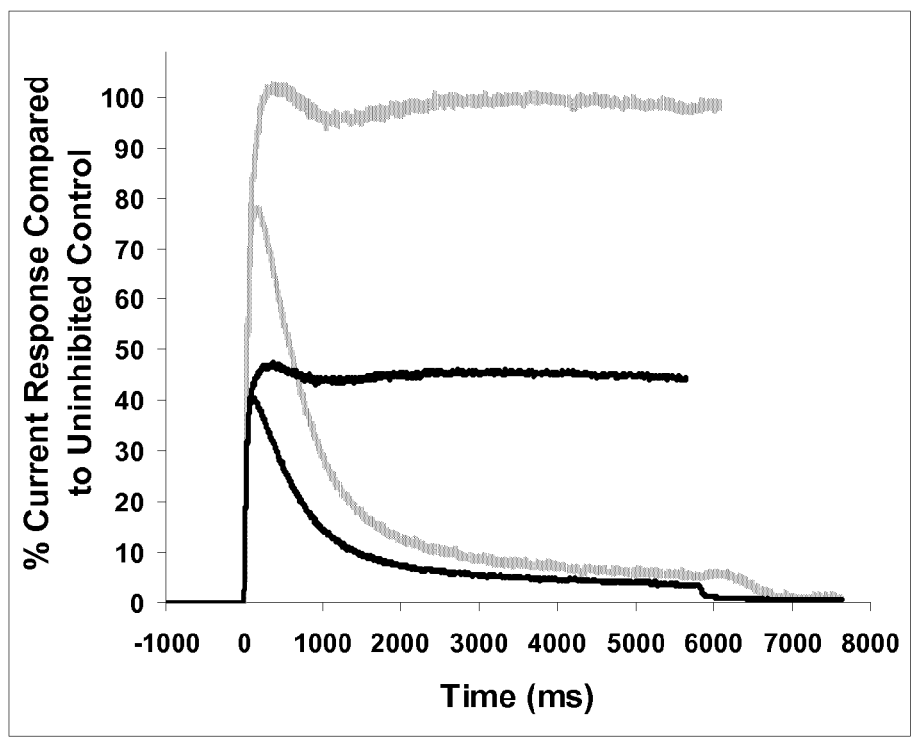
FIGS. 1A-B illustrate the inhibition of the muscle-type nicotinic acetylcholine receptor by the RNA aptamer, B55.
Figure 1B:
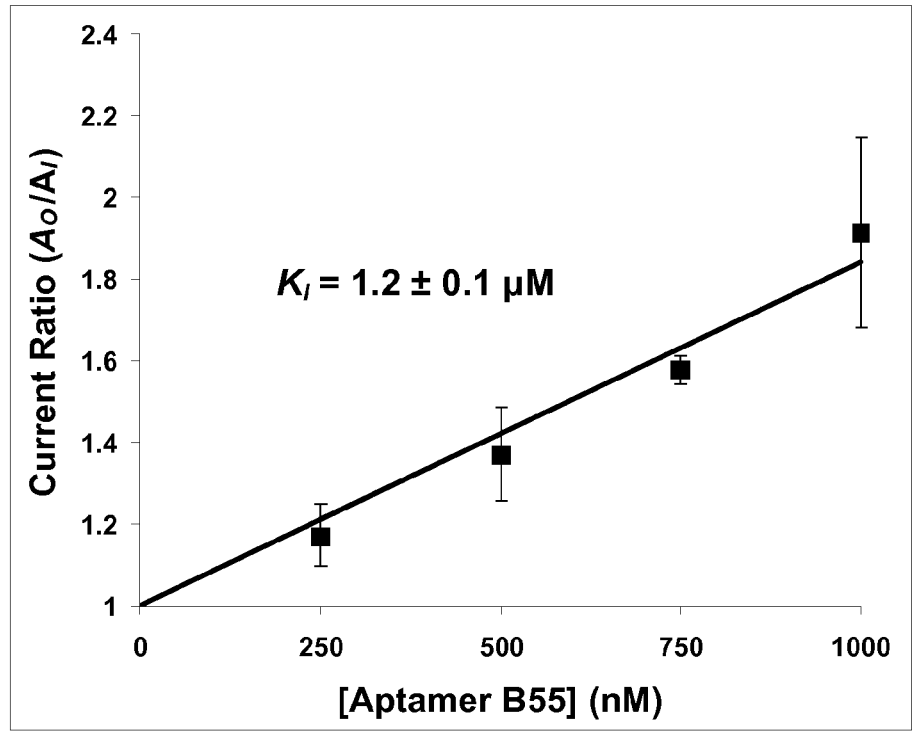

To explore the extent of similarity between the Aβ(1-40)-binding aptamers and the RNA aptamers that bind to the cocaine inhibitory site of the nicotinic acetylcholine receptor, the Aβ(1-40)-binding RNA aptamer (B55) with the highest affinity ($K_{d(amyloid)}$=29 nM) for the Aβ(1-40) peptide (Ylera et al., "Selection of RNA Aptamers to the Alzheimer's Disease Amyloid Peptide," Biochem. Biophys. Res. Commun. 290:1583-1588 (2002), which is hereby incorporated by reference in its entirety) was synthesized and used in cell-flow measurements to test for activity on nicotinic acetylcholine receptors expressed on the surface of BC$_3$H1 cells. The amyloid-peptide aptamer B55 inhibited carbamoylcholine-induced currents from the nicotinic acetylcholine receptor in a dose-dependent manner. The results of a typical experiment are shown in FIG. 1A. The apparent dissociation constant of the (β-amyloid-specific aptamer B55 from the nicotinic acetylcholine receptor is obtained from a plot of the data in FIG. 1B according to the equation $$\frac{A_O}{A_I} = 1 + \frac{[I]}{K_I}$$

(Hess et al., "Development and Application of Caged Ligands for Neurotransmitter Receptors in Transient Kinetic and Neuronal Circuit Mapping Studies," Methods Enzymol. 291:443 (1998), which is hereby incorporated by reference in its entirety). $A_O$ and $A_I$ represent the amplitudes of the current maxima obtained at a given concentration of activating ligand in the absence and presence of a noncompetitive inhibitor, respectively. [I] represents the inhibitor concentration and $K_I$ the observed dissociation constant of the inhibitor. The results in FIG. 1B indicate that aptamer, B55, inhibits the nicotinic acetylcholine receptor with an apparent $K_I$ value of 1.2±0.1 μM in the presence of 100-μM carbamoylcholine, an activating ligand for the nicotinic acetylcholine receptor. For comparison, in the presence of 100-μM carbamoylcholine, more than 50% of the nicotinic acetylcholine receptor activity is inhibited by 0.5 μM of an aptamer specifically isolated for binding to the cocaine-binding site of the nicotinic acetylcholine receptor (Hess et al., "Mechanism-Based Discovery of Ligands that Prevent Inhibition of the Nicotinic Acetylcholine Receptor by Cocaine and MK-801," Proc. Natl. Acad. Sci. U.S.A. 97:13895 (2000), which is hereby incorporated by reference in its entirety).

To further test the biological significance of the consensus sequence identified on the Aβ(1-40) aptamers and the nicotinic acetylcholine receptor aptamers, the capacity of the 7-nucleotide sequence to interact with and inhibit Aβ peptide aggregation was tested. Using the Thioflavin T assay, 500-μM of the common consensus sequence, UUCACCG, was found to abolish amyloid aggregation.

Thus, the similarity in consensus sequence reflects not only a structural similarity but also a functional similarity. This in turn indicates that a motif of the site on the Aβ(1-40) peptide to which the aptamers bind is similar to a motif of the cocaine-binding site of the nicotinic acetylcholine receptor to which the inhibitory Class I aptamers bind. Thus, ligands that bind to the site on the nicotinic acetylcholine receptor are likely to bind to the Aβ peptide and vice versa. Preliminary results using electrophoretic mobility shift indicate that cocaine binds to the Aβ(1-40) peptide (FIG. 3A-B).

The presence of a cocaine-binding site on amyloid peptides suggested agents which bind to the open channel conformation of the nicotinic acetylcholine receptor with a higher affinity than to the closed channel conformation and alleviate cocaine inhibition without inhibiting the receptor (Ulrich et al., "In Vitro Selection of RNA Molecules that Displace Cocaine from the Membrane-Bound Nicotinic Receptor," Proc. Natl. Acad. Sci. USA 95:14051-14056 (1998); Cui et al., "Selection of 2'-Fluoro-Modified RNA Aptamers for Alleviation of Cocaine and MK-801 Inhibition of the Nicotinic Acetylcholine Receptor," J. Membr. Biol. 202:137-149 (2004); Hess et al., "Reversing the Action of Noncompetitive Inhibitors (MK-801 and cocaine) on a Protein (Nicotinic Acetylcholine Receptor)-Mediated Reaction," *Biochemistry* 42:6106-6114 (2003), which are hereby incorporated by reference in their entirety) may also have an effect on the aggregation of amyloid peptides. FIG. 4A confirms that micromolar concentrations of a number of these cocaine-binding site ligands, namely ecgonine methyl ester, ecgonine, RTI 4220-70, and MK-801, inhibit aggregation of Aβ(1-40) in a dose-dependent manner as determined by use of the Thioflavin T fluorescence assay. Additional studies have shown similar cocaine-binding site ligands including RCS-III-140A, RCS-III-143A, RCS-III-202A, and RCS-III-218 also inhibit aggregation of the Aβ(1-40) peptide. In contrast, a closely related ligand, 3-acetoxy ecgonine methyl ester which does not alleviate cocaine inhibition of the nicotinic acetylcholine receptor does not inhibit aggregation of Aβ(1-40) (FIG. 4B).

Additional small organic compounds that are capable of binding to the cocaine-binding site of the nicotinic acetylcholine receptor likely affect the aggregation of the Aβ peptide as well. One such compound is phencyclidine (PCP). FIG. 5 demonstrates that 1 mM PCP abrogates Aβ aggregation, as determined using the Thioflavin T assay.

Ligands of the cocaine-binding site of the Aβ(1-40) peptide were also found to interact with the amyloid peptide with 42 residues [Aβ(1-42)]. Considering the nature of the two extra non-charged amino acids on the C terminus of the Aβ(1-42) peptide compared to the Aβ(1-40), a significant difference between the peptides in ligand-binding properties was not expected.

The concentration of the Aβ(1-40) peptide in the cerebrospinal fluid of patients with Alzheimer's Disease is ~0.004-~M (Southwick et al., "Assessment of Amyloid β Protein in Cerebrospinal Fluid as an Aid in the Diagnosis of Alzheimer's Disease," *J. Neurochem.* 66:259 (1996); Mehta et al., "Amyloid β Protein 1-40 and 1-42 Levels in Matched Cerebrospinal Fluid and Plasma from Patients with Alzheimer Disease," *Neurosci. Lett.* 304:102 (2001), which are hereby incorporated by reference in their entirety). This value can be used to approximate the concentration of the Aβ(1-40) peptide in the interstitial fluid of the brain. Based on the in vitro ability of ecgonine methyl ester and related compounds to inhibit Aβ(1-40) peptide aggregation, one may calculate an order-of-magnitude approximation of the concentration in brain tissue required to abolish Aβ aggregation in vivo. For example, from the results in FIG. 4A, one can calculate that the concentration of ecgonine methyl ester required to abolish the aggregation of Aβ(1-40) in the brain would be ~40 ng/g.

Cocaine and its derivatives including, ecgonine methyl ester, have been extensively studied by pharmacologists and anesthesiologists for decades. Ecgonine methyl ester is a particularly attractive lead candidate for the development of an Alzheimer's Disease therapeutic because of its low toxicity. High concentrations and large doses of ecgonine methyl ester have no effect on cardiovascular functions, in vitro up to 100 µM in cardiac myocytes (Crumb et al., "Characterization of the Sodium Channel Blocking Properties of the Major Metabolites of Cocaine in Single Cardiac Myocytes," *Pharmacol. Exp. Ther.* 261:910 (1992), which is hereby incorporated by reference in its entirety), or in vivo up to 1.5 mg/kg/min in i.v. infusion (anesthetized rats) (Erzouki et al., "Comparison of the Effects of Cocaine and its Metabolites on Cardiovascular Function in Anesthetized Rats," *Cardiovasc. Pharmacol.* 22:557 (1993), which is hereby incorporated by reference in its entirety) or up to 10 mg/kg as an i.v. bolus dose (Schindler et al., "Effects of Cocaine and Cocaine Metabolites on Cardiovascular Function in Squirrel Monkeys," *Eur. J. Pharmacol.* 431:53-59 (2001), which is hereby incorporated by reference in its entirety). Comparative toxicity studies of cocaine and its metabolites (including ecgonine methyl ester) have indicated that the lowest daily dose of ecgonine methyl ester required to elicit slight toxic manifestations is 298.2±49.6 mg/kg (conscious rats), with a corresponding brain tissue concentration of 478.43±57.89 µmg (Morishima et al., "The Comparative Toxicity of Cocaine and its Metabolites in Conscious Rats," *Anesthesiology* 90:1684 (1999), which is hereby incorporated by reference in its entirety). This is more than 10,000 times the estimated therapeutic concentration of ecgonine methyl ester (~40 ng/g). Therefore, this compound may have considerable potential as a lead in the development of a therapy for Alzheimer's Disease.

In summary, the sequence analysis of the nucleic acid aptamers that bind to Aβ(1-40) peptides with nanomolar affinity found a sequence of 7 nucleotides identical to that found in RNA aptamers that bind to a cocaine-specific inhibitory site of the muscle-type nicotinic acetylcholine receptor. As predicted from this observation, an RNA aptamer specific for the amyloid peptide also interacts with high affinity ($K_f$=1.2±0.1 µM) with the cocaine-specific inhibitory site (FIG. 1B) of the nicotinic acetylcholine receptor. More importantly, the 7-nucleotide consensus sequence alone is capable of interacting with and inhibiting Aβ peptide aggregation. In addition, cocaine binding site ligands of the nicotinic acetylcholine receptor also interact with Aβ(1-40) peptides and prevent aggregation of the Aβ(1-40) peptides.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A method of treating Alzheimer's Disease in a subject, said method comprising:

administering to the subject a compound having the following structure:

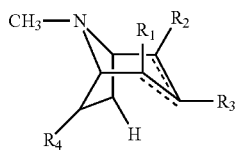

wherein
$R_1$ is H, —COOCH$_3$, or —COO$^-$Li$^+$; $R_2$ is carbonyl, —COOH, or —COOCH$_3$; $R_3$ is H, —OH, -Ph, or -PhCl; and $R_4$ is H or —S(O)$_2$Ph, wherein if $R_2$ is —COOCH$_3$ then $R_3$ is not H, conditions effective to treat or prevent Alzheimer's Disease in the subject.

2. The method according to claim 1, wherein said compound comprises a cocaine analogue selected from the group consisting of ecgonine, ecgonine methyl ester, RTI-4229-70, RCS-III-143, RCS-III-140A, RCS-III-218, and RCS-III-202A.

3. The method according to claim 1, wherein said administering is carried out orally, parenterally, nasally, subcutaneously, intravenously, intramuscularly, intraperitoneally, by implantation, by intracavitary or intravesical instillation, intraocularly, intraarterially, transdermally, or by application to mucous membranes.

4. The method according to claim 1, wherein the compound is administered with a pharmaceutically acceptable carrier.

5. The method according to claim 1, wherein the subject is a human.

6. A method of inhibiting aggregation of beta-amyloid peptides in a subject, said method comprising:

selecting a subject having an increased aggregation of beta-amyloid peptides as compared to a healthy subject and administering to the selected subject a compound having the following structure:

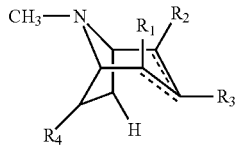

wherein

R₁ is H, —COOCH₃, or —COO⁻Li⁺; R₂ is carbonyl, —COOH, or —COOCH₃; R₃ is H, —OH, -Ph, or -PhCl; and R₄ is H or —S(O)₂Ph, wherein if R₂ is —COOCH₃ then R₃ is not H, under conditions effective to inhibit aggregation of beta-amyloid peptides in the subject.

7. The method according to claim 6, wherein said compound comprises a cocaine analogue selected from the group consisting of ecgonine, ecgonine methyl ester, RTI-4229-70, RCS-III-143, RCS-III-140A, RCS-III-218, and RCS-III-202A.

8. The method according to claim 6, wherein said beta-amyloid peptide is selected from the group consisting of beta-amyloid peptide Aβ(1-40) and beta-amyloid peptide Aβ(1-42).

9. The method according to claim 6, wherein said administering is carried out orally, parenterally, nasally, subcutaneously, intravenously, intramuscularly, intraperitoneally, by implantation, by intracavitary or intravesical instillation, intraocularly, intraarterially, transdermally, or by application to mucous membranes.

10. The method according to claim 6, wherein the compound is administered with a pharmaceutically acceptable carrier.

11. The method according to claim 6, wherein the subject is a human.

* * * * *

SEQUENCE LISTING

<160> NUMBER OF SEQ ID NOS: 95

<210> SEQ ID NO 1
<211> LENGTH: 4
<212> TYPE: RNA
<213> ORGANISM: Artificial
<220> FEATURE:
<223> OTHER INFORMATION: RNA Aptamer

<400> SEQUENCE: 1 accg                                                                      4

```
<210> SEQ ID NO 2
<211> LENGTH: 4
<212> TYPE: RNA
<213> ORGANISM: Artificial
<220> FEATURE:
<223> OTHER INFORMATION: RNA Aptamer

<400> SEQUENCE: 2 uccg                                                                       4

<210> SEQ ID NO 3
<211> LENGTH: 7
<212> TYPE: RNA
<213> ORGANISM: Artifical

<400> SEQUENCE: 3 uuuaccg                                                                    7

<210> SEQ ID NO 4
<211> LENGTH: 7
<212> TYPE: RNA
<213> ORGANISM: Artificial
<220> FEATURE:
<223> OTHER INFORMATION: RNA Aptamer

<400> SEQUENCE: 4 uucaccg                                                                    7

<210> SEQ ID NO 5
<211> LENGTH: 12
<212> TYPE: RNA
<213> ORGANISM: Artificial
<220> FEATURE:
<223> OTHER INFORMATION: RNA Aptamer

<400> SEQUENCE: 5
uucaccguaa gg                                                             12

<210> SEQ ID NO 6
<211> LENGTH: 12
<212> TYPE: RNA
<213> ORGANISM: Artificial
<220> FEATURE:
<223> OTHER INFORMATION: RNA Aptamer

<400> SEQUENCE: 6
aucaccguaa gg                                                             12

<210> SEQ ID NO 7
<211> LENGTH: 12
<212> TYPE: RNA
<213> ORGANISM: Artificial
<220> FEATURE:
<223> OTHER INFORMATION: RNA Aptamer

<400> SEQUENCE: 7
uuuaccguaa gg                                                             12

<210> SEQ ID NO 8
<211> LENGTH: 12
<212> TYPE: RNA
<213> ORGANISM: Artificial
<220> FEATURE:
<223> OTHER INFORMATION: RNA Aptamer

<400> SEQUENCE: 8
```
uuuuccguaa gg                                                        12

<210> SEQ ID NO 9
<211> LENGTH: 12
<212> TYPE: RNA
<213> ORGANISM: Artificial
<220> FEATURE:
<223> OTHER INFORMATION: RNA Aptamer

<400> SEQUENCE: 9
uuuaccguaa gg                                                        12

<210> SEQ ID NO 10
<211> LENGTH: 12
<212> TYPE: RNA
<213> ORGANISM: Artificial
<220> FEATURE:
<223> OTHER INFORMATION: RNA Aptamer

<400> SEQUENCE: 10
aucaccguaa gg                                                        12

<210> SEQ ID NO 11
<211> LENGTH: 12
<212> TYPE: RNA
<213> ORGANISM: Artificial
<220> FEATURE:
<223> OTHER INFORMATION: RNA Aptamer

<400> SEQUENCE: 11
uccaccguag au                                                        12

<210> SEQ ID NO 12
<211> LENGTH: 12
<212> TYPE: RNA
<213> ORGANISM: Artificial
<220> FEATURE:
<223> OTHER INFORMATION: RNA Aptamer

<400> SEQUENCE: 12
aucaccguaa gg                                                        12

<210> SEQ ID NO 13
<211> LENGTH: 12
<212> TYPE: RNA
<213> ORGANISM: Artificial
<220> FEATURE:
<223> OTHER INFORMATION: RNA Aptamer

<400> SEQUENCE: 13
uuuaccguaa gg                                                        12

<210> SEQ ID NO 14
<211> LENGTH: 12
<212> TYPE: RNA
<213> ORGANISM: Artificial
<220> FEATURE:
<223> OTHER INFORMATION: RNA Aptamer

<400> SEQUENCE: 14
uccaccguaa ga                                                        12

<210> SEQ ID NO 15
<211> LENGTH: 12
<212> TYPE: RNA
<213> ORGANISM: Artificial

```
<220> FEATURE:
<223> OTHER INFORMATION: RNA Aptamer

<400> SEQUENCE: 15
uccaccguaa ga                                                          12

<210> SEQ ID NO 16
<211> LENGTH: 12
<212> TYPE: RNA
<213> ORGANISM: Artificial
<220> FEATURE:
<223> OTHER INFORMATION: RNA Aptamer

<400> SEQUENCE: 16
uuuaccguaa gg                                                          12

<210> SEQ ID NO 17
<211> LENGTH: 12
<212> TYPE: RNA
<213> ORGANISM: Artificial
<220> FEATURE:
<223> OTHER INFORMATION: RNA Aptamer

<400> SEQUENCE: 17
uuuaccguaa gg                                                          12

<210> SEQ ID NO 18
<211> LENGTH: 12
<212> TYPE: RNA
<213> ORGANISM: Artificial
<220> FEATURE:
<223> OTHER INFORMATION: RNA Aptamer

<400> SEQUENCE: 18
uuuaccguaa gg                                                          12

<210> SEQ ID NO 19
<211> LENGTH: 12
<212> TYPE: RNA
<213> ORGANISM: Artificial
<220> FEATURE:
<223> OTHER INFORMATION: RNA Aptamer

<400> SEQUENCE: 19
uccaccguaa ga                                                          12

<210> SEQ ID NO 20
<211> LENGTH: 12
<212> TYPE: RNA
<213> ORGANISM: Artificial
<220> FEATURE:
<223> OTHER INFORMATION: RNA Aptamer

<400> SEQUENCE: 20
uuuuccguaa gg                                                          12

<210> SEQ ID NO 21
<211> LENGTH: 12
<212> TYPE: RNA
<213> ORGANISM: Artificial
<220> FEATURE:
<223> OTHER INFORMATION: RNA Aptamer

<400> SEQUENCE: 21
uccaccguaa ga                                                          12
```

```
<210> SEQ ID NO 22
<211> LENGTH: 12
<212> TYPE: RNA
<213> ORGANISM: Artificial
<220> FEATURE:
<223> OTHER INFORMATION: RNA Aptamer

<400> SEQUENCE: 22
uuuaccguaa gg                                                             12

<210> SEQ ID NO 23
<211> LENGTH: 12
<212> TYPE: RNA
<213> ORGANISM: Artificial
<220> FEATURE:
<223> OTHER INFORMATION: RNA Aptamer

<400> SEQUENCE: 23
aucaccguaa gg                                                             12

<210> SEQ ID NO 24
<211> LENGTH: 70
<212> TYPE: RNA
<213> ORGANISM: Artificial
<220> FEATURE:
<223> OTHER INFORMATION: RNA Aptamer

<400> SEQUENCE: 24
cucgaucacc guaaggacau cuacguaagu guaaugcggc uuguuuuccc caugcgucug          60
cauaucguu                                                                 70

<210> SEQ ID NO 25
<211> LENGTH: 67
<212> TYPE: RNA
<213> ORGANISM: Artificial
<220> FEATURE:
<223> OTHER INFORMATION: RNA Aptamer

<400> SEQUENCE: 25
uuuaccguaa ggccugucau cguuugacag cggcuuguug acccuuccac uaugugugcc          60
uguaaug                                                                   67

<210> SEQ ID NO 26
<211> LENGTH: 72
<212> TYPE: RNA
<213> ORGANISM: Artificial
<220> FEATURE:
<223> OTHER INFORMATION: RNA Aptamer

<400> SEQUENCE: 26
acuucgucuu gcagcgcggc uugucucuuc ccacauccgu ucuaucggua ugacucuuuu          60
uccguaaggu ca                                                             72

<210> SEQ ID NO 27
<211> LENGTH: 66
<212> TYPE: RNA
<213> ORGANISM: Artificial
<220> FEATURE:
<223> OTHER INFORMATION: RNA Aptamer

<400> SEQUENCE: 27
uuuaccguaa ggccugucuu cguuugacag cggcuuguug acccucacac uuuguaccuc          60
ugccug                                                                    66
```

<210> SEQ ID NO 28
<211> LENGTH: 69
<212> TYPE: RNA
<213> ORGANISM: Artificial
<220> FEATURE:
<223> OTHER INFORMATION: RNA Aptamer

<400> SEQUENCE: 28
cucgaucacc guaaggacau cuacauaagu guaaugcggc uuguuuuccc caugcaucug    60
cauaucugu                                                           69

<210> SEQ ID NO 29
<211> LENGTH: 66
<212> TYPE: RNA
<213> ORGANISM: Artificial
<220> FEATURE:
<223> OTHER INFORMATION: RNA Aptamer

<400> SEQUENCE: 29
uguccaccgu agauuguaaa cuaucgcgua aagcgaaguu uauguggcuu guuucccac    60 gccuug                                                              66

<210> SEQ ID NO 30
<211> LENGTH: 69
<212> TYPE: RNA
<213> ORGANISM: Artificial
<220> FEATURE:
<223> OTHER INFORMATION: RNA Aptamer

<400> SEQUENCE: 30
cucgaucacc guaaggacau uuacguaagu guaaugcggc uuguuuuccc caugcgucug    60
cauaucugu                                                           69

<210> SEQ ID NO 31
<211> LENGTH: 67
<212> TYPE: RNA
<213> ORGANISM: Artificial
<220> FEATURE:
<223> OTHER INFORMATION: RNA Aptamer

<400> SEQUENCE: 31
uuuaccguaa ggccugucuu cguuugacag cggcuuguug acccucacac uuuguaccug    60
cugccaa                                                             67

<210> SEQ ID NO 32
<211> LENGTH: 68
<212> TYPE: RNA
<213> ORGANISM: Artificial
<220> FEATURE:
<223> OTHER INFORMATION: RNA Aptamer

<400> SEQUENCE: 32
uccaccguaa gauuguaaac uaucggguaa agacgaaguu uauguggcuu guuucccacc    60
gccuugcc                                                            68

<210> SEQ ID NO 33
<211> LENGTH: 69
<212> TYPE: RNA
<213> ORGANISM: Artificial
<220> FEATURE:
<223> OTHER INFORMATION: RNA Aptamer

```
<400> SEQUENCE: 33 ugccaccgu aagauuguaa acuaucguaa agacgaaguu uauguggcuu guuuucccac    60
cgccuugcc                                                           69

<210> SEQ ID NO 34
<211> LENGTH: 67
<212> TYPE: RNA
<213> ORGANISM: Artificial
<220> FEATURE:
<223> OTHER INFORMATION: RNA Aptamer

<400> SEQUENCE: 34
uuuaccguaa ggccugucau cguuugacag cggcuuguug acccuuccac uaugugugcc    60
uguaaug                                                             67

<210> SEQ ID NO 35
<211> LENGTH: 66
<212> TYPE: RNA
<213> ORGANISM: Artificial
<220> FEATURE:
<223> OTHER INFORMATION: RNA Aptamer

<400> SEQUENCE: 35
uuuaccguaa ggccugucuu cguuugacag cggcuuguug acccacacac uuugucccgg    60
cugcag                                                              66

<210> SEQ ID NO 36
<211> LENGTH: 69
<212> TYPE: RNA
<213> ORGANISM: Artificial
<220> FEATURE:
<223> OTHER INFORMATION: RNA Aptamer

<400> SEQUENCE: 36
uuuaccguaa ggccugucuu cuuuugacag cggcuuguug acccucacgc uuugucccug    60
cuguaccug                                                           69

<210> SEQ ID NO 37
<211> LENGTH: 68
<212> TYPE: RNA
<213> ORGANISM: Artificial
<220> FEATURE:
<223> OTHER INFORMATION: RNA Aptamer

<400> SEQUENCE: 37
uccaccguaa gauuguaaac uaucgcguaa aagacgaagu uuauguggcu uguuuuccca    60
ccgccuug                                                            68

<210> SEQ ID NO 38
<211> LENGTH: 68
<212> TYPE: RNA
<213> ORGANISM: Artificial
<220> FEATURE:
<223> OTHER INFORMATION: RNA Aptamer

<400> SEQUENCE: 38
acuucgucuu gcagcgcggc uugucuuccc acauccguuc uaucgguaug acuuuuccg     60 uaagguca                                                            68

<210> SEQ ID NO 39
<211> LENGTH: 68
```

```
<212> TYPE: RNA
<213> ORGANISM: Artificial
<220> FEATURE:
<223> OTHER INFORMATION: RNA Aptamer

<400> SEQUENCE: 39
uccaccguaa gauuguaaac uaucgcguaa agacgaaguu uauguggcuu guucccacc    60 accuugcg                                                           68

<210> SEQ ID NO 40
<211> LENGTH: 67
<212> TYPE: RNA
<213> ORGANISM: Artificial
<220> FEATURE:
<223> OTHER INFORMATION: RNA Aptamer

<400> SEQUENCE: 40
uuuaccguaa ggccugucuu cguuugacag cggcuuguug acccucacgc uuugcccau    60 gcccguc                                                            67

<210> SEQ ID NO 41
<211> LENGTH: 70
<212> TYPE: RNA
<213> ORGANISM: Artificial
<220> FEATURE:
<223> OTHER INFORMATION: RNA Aptamer

<400> SEQUENCE: 41
cucgaucacc guaaggacau uuacguaagu guaaugcggc uuguuuuccc caugcguuug   60
cauaucugug                                                         70

<210> SEQ ID NO 42
<211> LENGTH: 40
<212> TYPE: RNA
<213> ORGANISM: Artificial
<220> FEATURE:
<223> OTHER INFORMATION: RNA Aptamer

<400> SEQUENCE: 42
acguugagua caaccccacc ccguucacgg uagcccugua                         40

<210> SEQ ID NO 43
<211> LENGTH: 39
<212> TYPE: RNA
<213> ORGANISM: Artificial
<220> FEATURE:
<223> OTHER INFORMATION: RNA Aptamer

<400> SEQUENCE: 43
gcuacaguac aacgggccgu guggaauaca ccgacaagg                          39

<210> SEQ ID NO 44
<211> LENGTH: 40
<212> TYPE: RNA
<213> ORGANISM: Artificial
<220> FEATURE:
<223> OTHER INFORMATION: RNA Aptamer

<400> SEQUENCE: 44
uccaccgauc uagaugaucc aggcacccga ccaccaccuc                         40

<210> SEQ ID NO 45
<211> LENGTH: 37
<212> TYPE: RNA
```

```
<213> ORGANISM: Artificial
<220> FEATURE:
<223> OTHER INFORMATION: RNA Aptamer

<400> SEQUENCE: 45
gcuuguggac caagaagcaa ccagucaccg uugcccc                                37

<210> SEQ ID NO 46
<211> LENGTH: 40
<212> TYPE: RNA
<213> ORGANISM: Artificial
<220> FEATURE:
<223> OTHER INFORMATION: RNA Aptamer

<400> SEQUENCE: 46
caacagaccu guguccguug aauccucuag auccagggug                             40

<210> SEQ ID NO 47
<211> LENGTH: 39
<212> TYPE: RNA
<213> ORGANISM: Artificial
<220> FEATURE:
<223> OTHER INFORMATION: RNA Aptamer

<400> SEQUENCE: 47 ggaccccca cagcaaguuu gccggcgacc gcguucuug                               39

<210> SEQ ID NO 48
<211> LENGTH: 40
<212> TYPE: RNA
<213> ORGANISM: Artificial
<220> FEATURE:
<223> OTHER INFORMATION: RNA Aptamer

<400> SEQUENCE: 48
cuugccacuc cugucuagcu ggcguagacc gcgcagaaag                             40

<210> SEQ ID NO 49
<211> LENGTH: 40
<212> TYPE: RNA
<213> ORGANISM: Artificial
<220> FEATURE:
<223> OTHER INFORMATION: RNA Aptamer

<400> SEQUENCE: 49
gcuaguagcc ucagcagcau aguuucgccg cuaugcagua                             40

<210> SEQ ID NO 50
<211> LENGTH: 40
<212> TYPE: RNA
<213> ORGANISM: Artificial
<220> FEATURE:
<223> OTHER INFORMATION: RNA Aptamer

<400> SEQUENCE: 50
uagcauaaug uggagcguug accggaccuc uccagucgua                             40

<210> SEQ ID NO 51
<211> LENGTH: 38
<212> TYPE: RNA
<213> ORGANISM: Artificial
<220> FEATURE:
<223> OTHER INFORMATION: RNA Aptamer

<400> SEQUENCE: 51
uggacuacgc acccgcuagu ccguccaaga acugugcg                               38
```

```
<210> SEQ ID NO 52
<211> LENGTH: 40
<212> TYPE: RNA
<213> ORGANISM: Artificial
<220> FEATURE:
<223> OTHER INFORMATION: RNA Aptamer

<400> SEQUENCE: 52
uucuguuccg accaauugaa uagucaccgu gaugauuuga                         40

<210> SEQ ID NO 53
<211> LENGTH: 39
<212> TYPE: RNA
<213> ORGANISM: Artificial
<220> FEATURE:
<223> OTHER INFORMATION: RNA Aptamer

<400> SEQUENCE: 53
gaugccagcg cgcauucuuc accgaaguac guauccacg                          39

<210> SEQ ID NO 54
<211> LENGTH: 39
<212> TYPE: RNA
<213> ORGANISM: Artificial
<220> FEATURE:
<223> OTHER INFORMATION: RNA Aptamer

<400> SEQUENCE: 54
uucgccgcug cacucucgca gcacuggucg ggauguguc                          39

<210> SEQ ID NO 55
<211> LENGTH: 6
<212> TYPE: RNA
<213> ORGANISM: Artificial
<220> FEATURE:
<223> OTHER INFORMATION: RNA Aptamer

<400> SEQUENCE: 55 gcugaa                                                               6

<210> SEQ ID NO 56
<211> LENGTH: 40
<212> TYPE: RNA
<213> ORGANISM: Artificial
<220> FEATURE:
<223> OTHER INFORMATION: RNA Aptamer

<400> SEQUENCE: 56
aguaggaaua cccccaucca aagcucgcua ggcugaacac                         40

<210> SEQ ID NO 57
<211> LENGTH: 40
<212> TYPE: RNA
<213> ORGANISM: Artificial
<220> FEATURE:
<223> OTHER INFORMATION: RNA Aptamer

<400> SEQUENCE: 57
gacggcccga gauugcagaa aaacgcgccc acgugucaga                         40

<210> SEQ ID NO 58
<211> LENGTH: 40
<212> TYPE: RNA
<213> ORGANISM: Artificial
<220> FEATURE:
```

<223> OTHER INFORMATION: RNA Aptamer

<400> SEQUENCE: 58
ucccuagcug acgauggauc uuggaucaca uaggcugcgc          40

<210> SEQ ID NO 59
<211> LENGTH: 38
<212> TYPE: RNA
<213> ORGANISM: Artificial
<220> FEATURE:
<223> OTHER INFORMATION: RNA Aptamer

<400> SEQUENCE: 59
ggacaugccg gucuugagcg gaggugaacc guaccacg          38

<210> SEQ ID NO 60
<211> LENGTH: 35
<212> TYPE: RNA
<213> ORGANISM: Artificial
<220> FEATURE:
<223> OTHER INFORMATION: RNA Aptamer

<400> SEQUENCE: 60
aacacgccuc aggacgccag gugaacccuc gaacc          35

<210> SEQ ID NO 61
<211> LENGTH: 39
<212> TYPE: RNA
<213> ORGANISM: Artificial
<220> FEATURE:
<223> OTHER INFORMATION: RNA Aptamer

<400> SEQUENCE: 61
aacgcugaau cccccgguca uagaacuuug auaguacag          39

<210> SEQ ID NO 62
<211> LENGTH: 40
<212> TYPE: RNA
<213> ORGANISM: Artificial
<220> FEATURE:
<223> OTHER INFORMATION: RNA Aptamer

<400> SEQUENCE: 62
uacugaauga ucuccacccg ccggaaugcg uauagucccu          40

<210> SEQ ID NO 63
<211> LENGTH: 40
<212> TYPE: RNA
<213> ORGANISM: Artificial
<220> FEATURE:
<223> OTHER INFORMATION: RNA Aptamer

<400> SEQUENCE: 63 gcugggaaa gcagguccgu ucccaccgcc ugaagcuuug          40

<210> SEQ ID NO 64
<211> LENGTH: 40
<212> TYPE: RNA
<213> ORGANISM: Artificial
<220> FEATURE:
<223> OTHER INFORMATION: RNA Aptamer

<400> SEQUENCE: 64
ccuccugaca caaccaccca accaccuucu ugaaacauuu          40

```
<210> SEQ ID NO 65
<211> LENGTH: 41
<212> TYPE: RNA
<213> ORGANISM: Artificial
<220> FEATURE:
<223> OTHER INFORMATION: RNA Aptamer

<400> SEQUENCE: 65
acaaccuuga uugcuugaaa ccucuaaccc gaggcucugu a                    41

<210> SEQ ID NO 66
<211> LENGTH: 5
<212> TYPE: RNA
<213> ORGANISM: Artificial
<220> FEATURE:
<223> OTHER INFORMATION: RNA Aptamer

<400> SEQUENCE: 66 gaaag                                                             5

<210> SEQ ID NO 67
<211> LENGTH: 34
<212> TYPE: RNA
<213> ORGANISM: Artificial
<220> FEATURE:
<223> OTHER INFORMATION: RNA Aptamer

<400> SEQUENCE: 67
cgaacgugga cgaagggcgg uuugugagug cuua                            34

<210> SEQ ID NO 68
<211> LENGTH: 41
<212> TYPE: RNA
<213> ORGANISM: Artificial
<220> FEATURE:
<223> OTHER INFORMATION: RNA Aptamer

<400> SEQUENCE: 68
cugacugcgu cucuauauga cauaggcgau gagaaagcag a                    41

<210> SEQ ID NO 69
<211> LENGTH: 41
<212> TYPE: RNA
<213> ORGANISM: Artificial
<220> FEATURE:
<223> OTHER INFORMATION: RNA Aptamer

<400> SEQUENCE: 69
ggaacagacg ucaucugugg cacguccgcu gcuagcagag a                    41

<210> SEQ ID NO 70
<211> LENGTH: 41
<212> TYPE: RNA
<213> ORGANISM: Artificial
<220> FEATURE:
<223> OTHER INFORMATION: RNA Aptamer

<400> SEQUENCE: 70
gacacaagcu ggaccacguc aagcguuuug ugaaagcagg u                    41

<210> SEQ ID NO 71
<211> LENGTH: 41
<212> TYPE: RNA
<213> ORGANISM: Artificial
<220> FEATURE:
<223> OTHER INFORMATION: RNA Aptamer
```

-continued

<400> SEQUENCE: 71
uggcaucuug ugcaugacaa cagaggguga aaccaacggg u                41

<210> SEQ ID NO 72
<211> LENGTH: 38
<212> TYPE: RNA
<213> ORGANISM: Artificial
<220> FEATURE:
<223> OTHER INFORMATION: RNA Aptamer

<400> SEQUENCE: 72
aaacuugccu ugguuuauaa cguaacaaua cagaacga                    38

<210> SEQ ID NO 73
<211> LENGTH: 38
<212> TYPE: RNA
<213> ORGANISM: Artificial
<220> FEATURE:
<223> OTHER INFORMATION: RNA Aptamer

<400> SEQUENCE: 73
agaaucuaag acgugaaaau gguaagacau ucucuacc                    38

<210> SEQ ID NO 74
<211> LENGTH: 40
<212> TYPE: RNA
<213> ORGANISM: Artificial
<220> FEATURE:
<223> OTHER INFORMATION: RNA Aptamer

<400> SEQUENCE: 74
aggugugcgc agacgaauag gguugugcga aagucuagca                  40

<210> SEQ ID NO 75
<211> LENGTH: 40
<212> TYPE: RNA
<213> ORGANISM: Artificial
<220> FEATURE:
<223> OTHER INFORMATION: RNA Aptamer

<400> SEQUENCE: 75
uuuagaguug aaaugcguaa ugguuaaaug auccauucug                  40

<210> SEQ ID NO 76
<211> LENGTH: 40
<212> TYPE: RNA
<213> ORGANISM: Artificial
<220> FEATURE:
<223> OTHER INFORMATION: RNA Aptamer

<400> SEQUENCE: 76
aacaaugcga ggguaaaagc auguucuaac cagggaggga                  40

<210> SEQ ID NO 77
<211> LENGTH: 36
<212> TYPE: RNA
<213> ORGANISM: Artificial
<220> FEATURE:
<223> OTHER INFORMATION: RNA Aptamer

<400> SEQUENCE: 77
auggaagccc uugauucuac ggaucuagcg agauuu                      36

<210> SEQ ID NO 78
<211> LENGTH: 39

```
<212> TYPE: RNA
<213> ORGANISM: Artificial
<220> FEATURE:
<223> OTHER INFORMATION: RNA Aptamer

<400> SEQUENCE: 78
ccuguaaggg cgaaacuaag cgagaaauca uuaggauga                               39

<210> SEQ ID NO 79
<211> LENGTH: 45
<212> TYPE: RNA
<213> ORGANISM: Artificial
<220> FEATURE:
<223> OTHER INFORMATION: RNA Aptamer

<400> SEQUENCE: 79
cucaaugcau acgcugguca acgggacgau uagugacaag gccgc                       45

<210> SEQ ID NO 80
<211> LENGTH: 39
<212> TYPE: RNA
<213> ORGANISM: Artificial
<220> FEATURE:
<223> OTHER INFORMATION: RNA Aptamer

<400> SEQUENCE: 80
aauaaguggc aaguagccua gagauuagaa gaccucaac                              39

<210> SEQ ID NO 81
<211> LENGTH: 41
<212> TYPE: RNA
<213> ORGANISM: Artificial
<220> FEATURE:
<223> OTHER INFORMATION: RNA Aptamer

<400> SEQUENCE: 81
aauugacgag cuggugggag auagucucag guaucuugug c                           41

<210> SEQ ID NO 82
<211> LENGTH: 38
<212> TYPE: RNA
<213> ORGANISM: Artificial
<220> FEATURE:
<223> OTHER INFORMATION: RNA Aptamer

<400> SEQUENCE: 82
gguggacagu aacuccuuag augcgguaga uucguagc                               38

<210> SEQ ID NO 83
<211> LENGTH: 40
<212> TYPE: RNA
<213> ORGANISM: Artificial
<220> FEATURE:
<223> OTHER INFORMATION: RNA Aptamer

<400> SEQUENCE: 83
uacgcgcuua ugauaaaggg uuagaaggac gagcgucgca                             40

<210> SEQ ID NO 84
<211> LENGTH: 39
<212> TYPE: RNA
<213> ORGANISM: Artificial
<220> FEATURE:
<223> OTHER INFORMATION: RNA Aptamer

<400> SEQUENCE: 84
```
cacaugcaga guaguguaag guaacaccca gguuuuuug                                      39

<210> SEQ ID NO 85
<211> LENGTH: 41
<212> TYPE: RNA
<213> ORGANISM: Artificial
<220> FEATURE:
<223> OTHER INFORMATION: RNA Aptamer

<400> SEQUENCE: 85
ccggggcgca ggugucccug acgaugauca auuucgggug a                                   41

<210> SEQ ID NO 86
<211> LENGTH: 39
<212> TYPE: RNA
<213> ORGANISM: Artificial
<220> FEATURE:
<223> OTHER INFORMATION: RNA Aptamer

<400> SEQUENCE: 86
gacgccuuua ugaaugacca gggaaguugu cagaagagg                                      39

<210> SEQ ID NO 87
<211> LENGTH: 38
<212> TYPE: RNA
<213> ORGANISM: Artificial
<220> FEATURE:
<223> OTHER INFORMATION: RNA Aptamer

<400> SEQUENCE: 87
gucacuuucu gaaugggaga uaucuucgau augguaau                                       38

<210> SEQ ID NO 88
<211> LENGTH: 6
<212> TYPE: RNA
<213> ORGANISM: Artificial
<220> FEATURE:
<223> OTHER INFORMATION: RNA Aptamer

<400> SEQUENCE: 88 guuaau                                                                           6

<210> SEQ ID NO 89
<211> LENGTH: 41
<212> TYPE: RNA
<213> ORGANISM: Artificial
<220> FEATURE:
<223> OTHER INFORMATION: RNA Aptamer

<400> SEQUENCE: 89
gaaggcgaaa ggcacaaaga ucugaugaag uuaauggauc a                                   41

<210> SEQ ID NO 90
<211> LENGTH: 35
<212> TYPE: RNA
<213> ORGANISM: Artificial
<220> FEATURE:
<223> OTHER INFORMATION: RNA Aptamer

<400> SEQUENCE: 90
guuaaucgcu gaauauucga agugcuuucc gugau                                          35

<210> SEQ ID NO 91
<211> LENGTH: 40
<212> TYPE: RNA
<213> ORGANISM: Artificial

```
<220> FEATURE:
<223> OTHER INFORMATION: RNA Aptamer

<400> SEQUENCE: 91
ugggcuuagg uguuaagucg augacuguuc auucucggua                              40

<210> SEQ ID NO 92
<211> LENGTH: 40
<212> TYPE: RNA
<213> ORGANISM: Artificial
<220> FEATURE:
<223> OTHER INFORMATION: RNA Aptamer

<400> SEQUENCE: 92
acgugagcga gcaauaaaag uccccugggg cggaguuaaa                              40

<210> SEQ ID NO 93
<211> LENGTH: 39
<212> TYPE: RNA
<213> ORGANISM: Artificial
<220> FEATURE:
<223> OTHER INFORMATION: RNA Aptamer

<400> SEQUENCE: 93
gggagagucu acggauccua gaaaaagcag gacguuauu                               39

<210> SEQ ID NO 94
<211> LENGTH: 42
<212> TYPE: RNA
<213> ORGANISM: Artificial
<220> FEATURE:
<223> OTHER INFORMATION: RNA Aptamer

<400> SEQUENCE: 94
caaaggggag ccacggggcg acguguaauc cucuauucag ca                          42

<210> SEQ ID NO 95
<211> LENGTH: 40
<212> TYPE: RNA
<213> ORGANISM: Artificial
<220> FEATURE:
<223> OTHER INFORMATION: RNA Aptamer

<400> SEQUENCE: 95
aaugaaggca auucuuuaac guuaauagga aggggguaaa                             40
```